US 7,745,395 B2

(12) United States Patent
Denmeade et al.

(10) Patent No.: US 7,745,395 B2
(45) Date of Patent: *Jun. 29, 2010

(54) PROAEROLYSIN CONTAINING PROTEASE ACTIVATION SEQUENCES AND METHODS OF USE FOR TREATMENT OF PROSTATE CANCER

(75) Inventors: Samuel R. Denmeade, Ellicott City, MD (US); John T. Isaacs, Phoenix, MD (US); J. Thomas Buckley, Victoria (CA)

(73) Assignees: University of Victoria Innovatiion and Development Corporation, Victoria, BC (CA); The Johns Hopkins University, Baltimore, MD (US)

( * ) Notice: Subject to any disclaimer, the term of this patent is extended or adjusted under 35 U.S.C. 154(b) by 458 days.

This patent is subject to a terminal disclaimer.

(21) Appl. No.: 11/856,543

(22) Filed: Sep. 17, 2007

(65) Prior Publication Data
US 2008/0089869 A1    Apr. 17, 2008

Related U.S. Application Data

(62) Division of application No. 10/487,115, filed as application No. PCT/US02/27061 on Aug. 23, 2002, now Pat. No. 7,282,476.

(60) Provisional application No. 60/314,613, filed on Aug. 24, 2001.

(51) Int. Cl.
A61K 38/16    (2006.01)
A61K 39/00    (2006.01)
C07K 14/195   (2006.01)
C07K 19/00    (2006.01)
C12N 15/62    (2006.01)

(52) U.S. Cl. .......................... 514/2; 435/69.7; 536/23.4; 536/23.7

(58) Field of Classification Search .................. None
See application file for complete search history.

(56) References Cited

U.S. PATENT DOCUMENTS

| | | | |
|---|---|---|---|
| 5,599,686 A | 2/1997 | DeFeo-Jones et al. | |
| 5,677,274 A | 10/1997 | Leppla et al. | |
| 5,777,078 A | 7/1998 | Bayley et al. | |
| 5,798,218 A | 8/1998 | Buckley | |
| 5,817,771 A | 10/1998 | Bayley et al. | |
| 5,824,776 A | 10/1998 | Bayley et al. | |
| 5,858,358 A | 1/1999 | June et al. | |
| 5,866,679 A | 2/1999 | DeFeo-Jones et al. | |
| 5,948,750 A | 9/1999 | Garsky et al. | |
| 5,985,877 A | 11/1999 | Dionne et al. | |
| 5,998,362 A | 12/1999 | Feng et al. | |
| 6,143,864 A | 11/2000 | DeFeo-Jones et al. | |
| 6,180,356 B1 * | 1/2001 | London et al. | 435/7.2 |
| 6,190,657 B1 | 2/2001 | Pawelek et al. | |
| 6,265,540 B1 | 7/2001 | Isaacs et al. | |
| 6,331,415 B1 | 12/2001 | Cabilly et al. | |
| 6,368,598 B1 | 4/2002 | D'Amico et al. | |
| 6,391,305 B1 | 5/2002 | Feng et al. | |
| 6,410,514 B1 | 6/2002 | Isaacs et al. | |
| 6,495,315 B2 | 12/2002 | Hildreth et al. | |
| 6,504,014 B1 | 1/2003 | Isaacs et al. | |
| 6,545,131 B1 | 4/2003 | Isaacs et al. | |
| 6,593,095 B1 | 7/2003 | Buckley et al. | |
| 7,053,042 B1 | 5/2006 | Denmeade et al. | |
| 7,094,750 B2 * | 8/2006 | Yu et al. | 514/2 |
| 7,456,146 B2 * | 11/2008 | Yu et al. | 514/2 |
| 2002/0041880 A1 | 4/2002 | DeFeo-Jones et al. | |
| 2002/0045736 A1 | 4/2002 | Yu et al. | |
| 2002/0077454 A1 | 6/2002 | Yu et al. | |
| 2005/0266512 A1 | 12/2005 | Buckley | |

FOREIGN PATENT DOCUMENTS

| | | |
|---|---|---|
| EP | 1 052 287 A2 | 11/2000 |
| EP | 1 052 288 A1 | 11/2000 |
| WO | WO 94/25616 A1 | 11/1994 |
| WO | WO 95/26204 A1 | 10/1995 |
| WO | WO 96/02555 A1 | 2/1996 |
| WO | WO 96/20688 A2 | 7/1996 |
| WO | WO 97/40857 A1 | 11/1997 |
| WO | WO 98/18810 A1 | 5/1998 |
| WO | WO 98/20135 A2 | 5/1998 |
| WO | WO 98/11211 A2 | 9/1998 |
| WO | WO 98/37919 A1 | 9/1998 |

(Continued)

OTHER PUBLICATIONS

Abrami et al., "The Pore-Forming Toxin Proaerolysin is Activated by Furin," *J. Biol.Chem.* 273:32656-32661 (1998).

(Continued)

*Primary Examiner*—Nashaat T Nashed
*Assistant Examiner*—William W Moore
(74) *Attorney, Agent, or Firm*—Klarquist Sparkman, LLP

(57) ABSTRACT

Disclosed herein are modified proaerolysin (PA) peptide. In some examples, the proteins include a prostate-specific protease cleavage site and can further include a prostate-tissue-specific binding domain which functionally replaces the native PA binding domain. In other examples, the proteins include a furin cleavage site and a prostate tissue-specific binding domain which functionally replaces the native PA binding domain. Methods of using such peptides to treat prostate cancer are also disclosed.

30 Claims, 5 Drawing Sheets

FOREIGN PATENT DOCUMENTS

| WO | WO 98/40100 A1 | 9/1998 |
| --- | --- | --- |
| WO | WO 98/52581 A1 | 11/1998 |
| WO | WO 98/52966 A1 | 11/1998 |
| WO | WO 99/02175 A1 | 1/1999 |
| WO | WO 99/20252 A1 | 4/1999 |
| WO | WO 00/01419 A1 | 1/2000 |
| WO | WO 01/09165 A3 | 2/2001 |
| WO | WO 01/85777 A2 | 11/2001 |
| WO | WO 02/26777 A1 | 4/2002 |
| WO | WO 02/38799 A2 | 5/2002 |
| WO | WO 02/43773 A2 | 6/2002 |

OTHER PUBLICATIONS

Audtho et al., "Production of Chymotrypsin-Resistant *Bacillus thuringiensis* Cry2Aa1 δ-Endotoxin by Protein Engineering," *Appl. Environ. Micriobiol. 65*:4601-4605 (1999).

Ballard et al., "The Primary Structure of *Clostridium septicum* Alpha-Toxin Exhibits Similarity with That of *Aeromonas hydrophila* Aerolysin," *Infect. Immun*. 63:340-344 (1995).

Chen et al., "Glycophosphatidylinositol-Anchored Protein Deficiency as a Marker of *Mutator* Phenotypes in Cancer," *Cancer Res. 61*:654-658 (2001).

Correale et al., "Generation of Human Cytolytic T Lymphocyte Lines Directed Against Prostate-Specific Antigen (PSA) Employing a PSA Oligoepitope Peptide," *J. Immunol. 161*:3186-3194 (1998).

Denmeade et al., "Specific and Efficient Peptide Substrates for Assaying the Proteolytic Activity of Prostate-Specific Antigen," *Cancer Res*. 57:4924-4930 (1997).

Gong et al., "Overview of Evolving Strategies Incorporating Prostate-Specific Membrane Antigen as Target for Therapy," *Mol. Urol*. 4:217-222 (2000).

Gordon et al., "*Clostridium septicum* Alpha-Toxin Is Proteolytically Activated by Furin," *Infect. Immun*. 65:4130-4134 (1997).

MacKenzie et al., "Analysis of Receptor Binding by the Channel-Forming Toxin Aerolysin Using Surface Plasmon Resonance," *J. Biol. Chem. 274*:22604-22609 (1999).

Pang et al., "Activation and Fragmentation of *Bacillus thuringiensis* δ-Endotoxin by High Concentrations of Proteolytic Enzymes," *Can. J. Microbiol*. 45:816-825 (1999).

Rosen et al. "Enzymatic Activation of a Modified Proaerolysin Toxin by Prostate-Specific Antigen (PSA) as Treatment for Prostate Cancer," *Proceedings of the American Association for Cancer Research Annual Meeting 43*:92 (2002).

Rossjohn et al., "Aerolysin and Pertussis Toxin Share a Common Receptor-Binding Domain," *EMBO J. 16*:3426-3434 (1997).

Spyres et al., "Cytosolic Delivery and Characterization of the TcdB Glucosylating Domain by Using a Heterologous Protein Fusion," *Infection Immun*. 69:599-601 (2001).

Tanha et al., "Optimal Design Features of Camelized Human Single-Domain Antibody Libraries," *J. Biol. Chem. 276*:24774-24780 (2001).

Walker and Bayley, "A Pore-Forming Protein with a Protease-Activated Trigger," *Protein Eng. 7*:91-97 (1994).

Williams et al, "Tumoricidal Effects of a PSA-Activated Pore-Forming Toxin," *Proceedings of the American Association for Cancer Research 46*:1446 (2005).

Barry et al., "The Channel-Forming Protein Proaerolysin Remains a Dimer at Low Concentrations in Solution," *J. Biol. Chem. 276*:551-554, 2001.

* cited by examiner

FIG. 1

Proaerolysin

| Binding Domain | Toxin | Furin Cleavage Site (KVRRAR) | Inhibitory Peptide |

↓ Cleavage by Furin
Removes Inhibitory Peptide

Aerolysin

| Binding Domain | Toxin | Furin Cleavage Site (KVRR) |

↓ Aerolysin inserts into the cell membrane, forming pores

Cell Death

FIG. 2

[Bar chart: % of Total Hemolysis vs Concentration of PSA-Proaerolysin (PSA-PA1) at 10nM, 5nM, 1nM. Legend: 50% Plasma, 50% Plasma + PSA, Control (PSA in Buffer). At 10nM, 50% Plasma + PSA ≈ 43%; at 5nM ≈ 11%; at 1nM ≈ 0.]

FIG. 5A: Wild-type Proaerolysin (SEQ ID NOS: 1 and 2)

| Binding Domain | Toxin | Furin Cleavage Site (KVRRAR) | Inhibitory Peptide |
|---|---|---|---|

FIG. 5B: Example of a Variant Proaerolysin (SEQ ID NOS: 3 and 4)

| Binding Domain | Toxin | Prostate-Specific Protease Cleavage Site (e.g. HSSKLQ) | Inhibitory Peptide |
|---|---|---|---|

FIG. 5C Example of a Variant Proaerolysin

| Binding Domain | Toxin | Mutated Furin Cleavage Site (i.e. AAAAAA) | Inhibitory Peptide |
|---|---|---|---|

Protease-Specific Cleavage Site  or  Protease-Specific Cleavage Site  or  Protease-Specific Cleavage Site

FIG. 5D Example of a Variant Proaerolysin with a Functionally Deleted Binding Domain

| Mutated Binding Domain * | Toxin | Prostate-Specific Protease Cleavage Site (e.g. HSSKLQ) | Inhibitory Peptide |
|---|---|---|---|

FIG. 5E Example of a Variant Proaerolysin with a Functionally Replaced Binding Domain

| Mutated Binding Domain * | Toxin | Prostate-Specific Protease Cleavage Site (e.g. HSSKLQ) | Inhibitory Peptide |
|---|---|---|---|

Prostate Tissue Specific Binding Domain (e.g. LHRH)   and/or   Prostate Tissue Specific Binding Domain (e.g. LHRH)

Insertion at modified PA N-terminus        Insertion at modified PA C-terminus

FIG. 5F Example of a Variant Proaerolysin with a Functionally Replaced Binding Domain

| Mutated Binding Domain * | Toxin Y215C A300C | Prostate-Specific Protease Cleavage Site (e.g. HSSKLQ) | Inhibitory Peptide |
|---|---|---|---|

| Prostate Tissue Specific Binding Domain (e.g. LHRH) | and/or | Prostate Tissue Specific Binding Domain (e.g. LHRH) |
|---|---|---|

Attachment at modified PA amino acid Y215    Attachment at modified PA amino acid A300

FIG. 5G Example of a Variant Proaerolysin with a Functionally Deleted Binding Domain (Amino acids 1-83 deleted)

| Toxin | Prostate-Specific Protease Cleavage Site (e.g. HSSKLQ) | Inhibitory Peptide |
|---|---|---|

FIG. 5H Example of a Variant Proaerolysin with Functionally Replaced Binding Domain

| Toxin | Prostate-Specific Protease Cleavage Site (e.g. HSSKLQ) | Inhibitory Peptide |
|---|---|---|

| Prostate Tissue Specific Binding Domain (e.g. LHRH) | and/or | Prostate Tissue Specific Binding Domain (e.g. LHRH) |
|---|---|---|

Insertion at modified PA N-terminus    Insertion at modified PA C-terminus

FIG. 5I Example of a Variant Proaerolysin with a Functionally Replaced Binding Domain

| Toxin Y215C A300C | Prostate-Specific Protease Cleavage Site (e.g. HSSKLQ) | Inhibitory Peptide |
|---|---|---|

| Prostate Tissue Specific Binding Domain (e.g. LHRH) | and/or | Prostate Tissue Specific Binding Domain (e.g. LHRH) |
|---|---|---|

Attachment at modified PA amino acid Y215    Attachment at modified PA amino acid A300

FIG. 5J Example of a Variant Proaerolysin with a Functionally Replaced Binding Domain

| Mutated Binding Domain * | Toxin | Furin Cleavage Site | Inhibitory Peptide |
|---|---|---|---|

| Prostate Tissue Specific Binding Domain (e.g. LHRH) | and/or | Prostate Tissue Specific Binding Domain (e.g. LHRH) |
|---|---|---|

Insertion at modified PA N-terminus  Insertion at modified PA C-terminus

FIG. 5K Example of a Variant Proaerolysin with a Functionally Replaced Binding Domain

| Mutated Binding Domain * | Toxin Y215C A300C | Furin Cleavage Site | Inhibitory Peptide |
|---|---|---|---|

| Prostate Tissue Specific Binding Domain (e.g. LHRH) | and/or | Prostate Tissue Specific Binding Domain (e.g. LHRH) |
|---|---|---|

Attachment at modified PA amino acid Y215    Attachment at modified PA amino acid A300

FIG. 5L Example of a Variant Proaerolysin with Functionally Replaced Binding Domain

| Toxin | Furin Cleavage Site | Inhibitory Peptide |
|---|---|---|

| Prostate Tissue Specific Binding Domain (e.g. LHRH) | and/or | Prostate Tissue Specific Binding Domain (e.g. LHRH) |
|---|---|---|

Insertion at modified PA N-terminus    Insertion at modified PA C-terminus

FIG. 5M Example of a Variant Proaerolysin with a Functionally Replaced Binding Domain

| Toxin Y215C A300C | Furin Cleavage Site | Inhibitory Peptide |
|---|---|---|

| Prostate Tissue Specific Binding Domain (e.g. LHRH) | and/or | Prostate Tissue Specific Binding Domain (e.g. LHRH) |
|---|---|---|

Attachment at modified PA amino acid Y215    Attachment at modified PA amino acid A300

SEQUENCE LISTING

```
<160> NUMBER OF SEQ ID NOS: 25

<210> SEQ ID NO 1
<211> LENGTH: 1410
```

US 7,745,395 B2
41                                      42
-continued

```
<212> TYPE: DNA
<213> ORGANISM: Aeromonas hydrophilia
<220> FEATURE:
<221> NAME/KEY: CDS
<222> LOCATION: (1)..(1410)

<400> SEQUENCE: 1 gca gag ccc gtc tat cca gac cag ctt cgc ttg ttt tca ttg ggc caa         48
Ala Glu Pro Val Tyr Pro Asp Gln Leu Arg Leu Phe Ser Leu Gly Gln
1               5                   10                  15 ggg gtc tgt ggc gac aag tat cgc ccc gtc aat cga gaa gaa gcc caa         96
Gly Val Cys Gly Asp Lys Tyr Arg Pro Val Asn Arg Glu Glu Ala Gln
            20                  25                  30 agc gtt aaa agc aat att gtc ggc atg atg ggg caa tgg caa ata agc        144
Ser Val Lys Ser Asn Ile Val Gly Met Met Gly Gln Trp Gln Ile Ser
        35                  40                  45 ggg ctg gcc aac ggc tgg gtc att atg ggg ccg ggt tat aac ggt gaa        192
Gly Leu Ala Asn Gly Trp Val Ile Met Gly Pro Gly Tyr Asn Gly Glu
    50                  55                  60 ata aaa cca ggg aca gcg tcc aat acc tgg tgt tat ccg acc aat cct        240
Ile Lys Pro Gly Thr Ala Ser Asn Thr Trp Cys Tyr Pro Thr Asn Pro
65                  70                  75                  80 gtt acc ggt gaa ata ccg aca ctg tct gcc ctg gat att cca gat ggt        288
Val Thr Gly Glu Ile Pro Thr Leu Ser Ala Leu Asp Ile Pro Asp Gly
                85                  90                  95 gac gaa gtc gat gtg cag tgg cga ctg gta cat gac agt gcg aat ttc        336
Asp Glu Val Asp Val Gln Trp Arg Leu Val His Asp Ser Ala Asn Phe
            100                 105                 110 atc aaa cca acc agc tat ctg gcc cat tac ctc ggt tat gcc tgg gtg        384
Ile Lys Pro Thr Ser Tyr Leu Ala His Tyr Leu Gly Tyr Ala Trp Val
        115                 120                 125 ggc ggc aat cac agc caa tat gtc ggc gaa gac atg gat gtg acc cgt        432
Gly Gly Asn His Ser Gln Tyr Val Gly Glu Asp Met Asp Val Thr Arg
    130                 135                 140 gat ggc gac ggc tgg gtg atc cgt ggc aac aat gac ggc ggc tgt gac        480
Asp Gly Asp Gly Trp Val Ile Arg Gly Asn Asn Asp Gly Gly Cys Asp
145                 150                 155                 160 ggc tat cgc tgt ggt gac aag acg gcc atc aag gtc agc aac ttc gcc        528
Gly Tyr Arg Cys Gly Asp Lys Thr Ala Ile Lys Val Ser Asn Phe Ala
                165                 170                 175 tat aac ctg gat ccc gac agc ttc aag cat ggc gat gtc acc cag tcc        576
Tyr Asn Leu Asp Pro Asp Ser Phe Lys His Gly Asp Val Thr Gln Ser
            180                 185                 190 gac cgc cag ctg gtc aag act gtg gtg ggc tgg gcg gtc aac gac agc        624
Asp Arg Gln Leu Val Lys Thr Val Val Gly Trp Ala Val Asn Asp Ser
        195                 200                 205 gac acc ccc caa tcc ggc tat gac gtc acc ctg cgc tac gac aca gcc        672
Asp Thr Pro Gln Ser Gly Tyr Asp Val Thr Leu Arg Tyr Asp Thr Ala
    210                 215                 220 acc aac tgg tcc aag acc aac acc tat ggc ctg agc gag aag gtg acc        720
Thr Asn Trp Ser Lys Thr Asn Thr Tyr Gly Leu Ser Glu Lys Val Thr
225                 230                 235                 240 acc aag aac aag ttc aag tgg cca ctg gtg ggg gaa acc caa ctc tcc        768
Thr Lys Asn Lys Phe Lys Trp Pro Leu Val Gly Glu Thr Gln Leu Ser
                245                 250                 255 atc gag att gct gcc aat cag tcc tgg gcg tcc cag aac ggg ggc tcg        816
Ile Glu Ile Ala Ala Asn Gln Ser Trp Ala Ser Gln Asn Gly Gly Ser
            260                 265                 270 acc acc acc tcc ctg tct cag tcc gtg cga ccg act gtg ccg gcc cgc        864
Thr Thr Thr Ser Leu Ser Gln Ser Val Arg Pro Thr Val Pro Ala Arg
        275                 280                 285
```

```
tcc aag atc ccg gtg aag ata gag ctc tac aag gcc gac atc tcc tat         912
Ser Lys Ile Pro Val Lys Ile Glu Leu Tyr Lys Ala Asp Ile Ser Tyr
    290                 295                 300 ccc tat gag ttc aag gcc gat gtc agc tat gac ctg acc ctg agc ggc         960
Pro Tyr Glu Phe Lys Ala Asp Val Ser Tyr Asp Leu Thr Leu Ser Gly
305                 310                 315                 320 ttc ctg cgc tgg ggc ggc aac gcc tgg tat acc cac ccg gac aac cgt        1008
Phe Leu Arg Trp Gly Gly Asn Ala Trp Tyr Thr His Pro Asp Asn Arg
                325                 330                 335 ccg aac tgg aac cac acc ttc gtc ata ggt ccg tac aag gac aag gcg        1056
Pro Asn Trp Asn His Thr Phe Val Ile Gly Pro Tyr Lys Asp Lys Ala
            340                 345                 350 agc agc att cgg tac cag tgg gac aag cgt tac atc ccg ggt gaa gtg        1104
Ser Ser Ile Arg Tyr Gln Trp Asp Lys Arg Tyr Ile Pro Gly Glu Val
        355                 360                 365 aag tgg tgg gac tgg aac tgg acc ata cag cag aac ggt ctg tct acc        1152
Lys Trp Trp Asp Trp Asn Trp Thr Ile Gln Gln Asn Gly Leu Ser Thr
    370                 375                 380 atg cag aac aac ctg gcc aga gtg ctg cgc ccg gtg cgg gcg ggg atc        1200
Met Gln Asn Asn Leu Ala Arg Val Leu Arg Pro Val Arg Ala Gly Ile
385                 390                 395                 400 acc ggt gat ttc agt gcc gag agc cag ttt gcc ggc aac ata gag atc        1248
Thr Gly Asp Phe Ser Ala Glu Ser Gln Phe Ala Gly Asn Ile Glu Ile
                405                 410                 415 ggt gct ccc gtg ccg ctc gcg gct gac agc aag gtg cgt cgt gct cgc        1296
Gly Ala Pro Val Pro Leu Ala Ala Asp Ser Lys Val Arg Arg Ala Arg
            420                 425                 430 agt gtg gac ggc gct ggt caa ggc ctg agg ctg gag atc ccg ctc gat        1344
Ser Val Asp Gly Ala Gly Gln Gly Leu Arg Leu Glu Ile Pro Leu Asp
        435                 440                 445 gcg caa gag ctc tcc ggg ctt ggc ttc aac aac gtc agc ctc agc gtg        1392
Ala Gln Glu Leu Ser Gly Leu Gly Phe Asn Asn Val Ser Leu Ser Val
    450                 455                 460 acc cct gct gcc aat caa                                                1410
Thr Pro Ala Ala Asn Gln
465                 470

<210> SEQ ID NO 2
<211> LENGTH: 470
<212> TYPE: PRT
<213> ORGANISM: Aeromonas hydrophilia

<400> SEQUENCE: 2

Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
                20                  25                  30

Ser Val Lys Ser Asn Ile Val Gly Met Met Gly Gln Trp Gln Ile Ser
            35                  40                  45

Gly Leu Ala Asn Gly Trp Val Ile Met Gly Pro Gly Tyr Asn Gly Glu
        50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
                100                 105                 110

Ile Lys Pro Thr Ser Tyr Leu Ala His Tyr Leu Gly Tyr Ala Trp Val
```

```
                115                 120                 125
Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Val Gly Trp Ala Val Asn Asp Ser
        195                 200                 205

Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Gln Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
        275                 280                 285

Ser Lys Ile Pro Val Lys Ile Glu Leu Tyr Lys Ala Asp Ile Ser Tyr
    290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala
            340                 345                 350

Ser Ser Ile Arg Tyr Gln Trp Asp Lys Arg Tyr Ile Pro Gly Glu Val
        355                 360                 365

Lys Trp Trp Asp Trp Asn Trp Thr Ile Gln Gln Asn Gly Leu Ser Thr
    370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Leu Ala Ala Asp Ser Lys Val Arg Arg Ala Arg
            420                 425                 430

Ser Val Asp Gly Ala Gly Gln Gly Leu Arg Leu Glu Ile Pro Leu Asp
        435                 440                 445

Ala Gln Glu Leu Ser Gly Leu Gly Phe Asn Asn Val Ser Leu Ser Val
    450                 455                 460

Thr Pro Ala Ala Asn Gln
465                 470

<210> SEQ ID NO 3
<211> LENGTH: 1410
<212> TYPE: DNA
<213> ORGANISM: Artificial Sequence
<220> FEATURE:
<223> OTHER INFORMATION: Proaerolysin with a PSA sequence substituted
      for the furin site.
<220> FEATURE:
<221> NAME/KEY: CDS
<222> LOCATION: (1)..(1410)
```

<400> SEQUENCE: 3

```
gca gag ccc gtc tat cca gac cag ctt cgc ttg ttt tca ttg ggc caa      48
Ala Glu Pro Val Tyr Pro Asp Gln Leu Arg Leu Phe Ser Leu Gly Gln
1               5                   10                  15 ggg gtc tgt ggc gac aag tat cgc ccc gtc aat cga gaa gaa gcc caa      96
Gly Val Cys Gly Asp Lys Tyr Arg Pro Val Asn Arg Glu Glu Ala Gln
            20                  25                  30 agc gtt aaa agc aat att gtc ggc atg atg ggg caa tgg caa ata agc     144
Ser Val Lys Ser Asn Ile Val Gly Met Met Gly Gln Trp Gln Ile Ser
        35                  40                  45 ggg ctg gcc aac ggc tgg gtc att atg ggg ccg ggt tat aac ggt gaa     192
Gly Leu Ala Asn Gly Trp Val Ile Met Gly Pro Gly Tyr Asn Gly Glu
    50                  55                  60 ata aaa cca ggg aca gcg tcc aat acc tgg tgt tat ccg acc aat cct     240
Ile Lys Pro Gly Thr Ala Ser Asn Thr Trp Cys Tyr Pro Thr Asn Pro
65                  70                  75                  80 gtt acc ggt gaa ata ccg aca ctg tct gcc ctg gat att cca gat ggt     288
Val Thr Gly Glu Ile Pro Thr Leu Ser Ala Leu Asp Ile Pro Asp Gly
                85                  90                  95 gac gaa gtc gat gtg cag tgg cga ctg gta cat gac agt gcg aat ttc     336
Asp Glu Val Asp Val Gln Trp Arg Leu Val His Asp Ser Ala Asn Phe
            100                 105                 110 atc aaa cca acc agc tat ctg gcc cat tac ctc ggt tat gcc tgg gtg     384
Ile Lys Pro Thr Ser Tyr Leu Ala His Tyr Leu Gly Tyr Ala Trp Val
        115                 120                 125 ggc ggc aat cac agc caa tat gtc ggc gaa gac atg gat gtg acc cgt     432
Gly Gly Asn His Ser Gln Tyr Val Gly Glu Asp Met Asp Val Thr Arg
    130                 135                 140 gat ggc gac ggc tgg gtg atc cgt ggc aac aat gac ggc ggc tgt gac     480
Asp Gly Asp Gly Trp Val Ile Arg Gly Asn Asn Asp Gly Gly Cys Asp
145                 150                 155                 160 ggc tat cgc tgt ggt gac aag acg gcc atc aag gtc agc aac ttc gcc     528
Gly Tyr Arg Cys Gly Asp Lys Thr Ala Ile Lys Val Ser Asn Phe Ala
                165                 170                 175 tat aac ctg gat ccc gac agc ttc aag cat ggc gat gtc acc cag tcc     576
Tyr Asn Leu Asp Pro Asp Ser Phe Lys His Gly Asp Val Thr Gln Ser
            180                 185                 190 gac cgc cag ctg gtc aag act gtg gtg ggc tgg gcg gtc aac gac agc     624
Asp Arg Gln Leu Val Lys Thr Val Val Gly Trp Ala Val Asn Asp Ser
        195                 200                 205 gac acc ccc caa tcc ggc tat gac gtc acc ctg cgc tac gac aca gcc     672
Asp Thr Pro Gln Ser Gly Tyr Asp Val Thr Leu Arg Tyr Asp Thr Ala
    210                 215                 220 acc aac tgg tcc aag acc aac acc tat ggc ctg agc gag aag gtg acc     720
Thr Asn Trp Ser Lys Thr Asn Thr Tyr Gly Leu Ser Glu Lys Val Thr
225                 230                 235                 240 acc aag aac aag ttc aag tgg cca ctg gtg ggg gaa acc caa ctc tcc     768
Thr Lys Asn Lys Phe Lys Trp Pro Leu Val Gly Glu Thr Gln Leu Ser
                245                 250                 255 atc gag att gct gcc aat cag tcc tgg gcg tcc cag aac ggg ggc tcg     816
Ile Glu Ile Ala Ala Asn Gln Ser Trp Ala Ser Gln Asn Gly Gly Ser
            260                 265                 270 acc acc acc tcc ctg tct cag tcc gtg cga ccg act gtg ccg gcc cgc     864
Thr Thr Thr Ser Leu Ser Gln Ser Val Arg Pro Thr Val Pro Ala Arg
        275                 280                 285 tcc aag atc ccg gtg aag ata gag ctc tac aag gcc gac atc tcc tat     912
Ser Lys Ile Pro Val Lys Ile Glu Leu Tyr Lys Ala Asp Ile Ser Tyr
    290                 295                 300
```

```
ccc tat gag ttc aag gcc gat gtc agc tat gac ctg acc ctg agc ggc        960
Pro Tyr Glu Phe Lys Ala Asp Val Ser Tyr Asp Leu Thr Leu Ser Gly
305                 310                 315                 320 ttc ctg cgc tgg ggc ggc aac gcc tgg tat acc cac ccg gac aac cgt       1008
Phe Leu Arg Trp Gly Gly Asn Ala Trp Tyr Thr His Pro Asp Asn Arg
                325                 330                 335 ccg aac tgg aac cac acc ttc gtc ata ggt ccg tac aag gac aag gcg       1056
Pro Asn Trp Asn His Thr Phe Val Ile Gly Pro Tyr Lys Asp Lys Ala
            340                 345                 350 agc agc att cgg tac cag tgg gac aag cgt tac atc ccg ggt gaa gtg       1104
Ser Ser Ile Arg Tyr Gln Trp Asp Lys Arg Tyr Ile Pro Gly Glu Val
        355                 360                 365 aag tgg tgg gac tgg aac tgg acc ata cag cag aac ggt ctg tct acc       1152
Lys Trp Trp Asp Trp Asn Trp Thr Ile Gln Gln Asn Gly Leu Ser Thr
    370                 375                 380 atg cag aac aac ctg gcc aga gtg ctg cgc ccg gtg cgg gcg ggg atc       1200
Met Gln Asn Asn Leu Ala Arg Val Leu Arg Pro Val Arg Ala Gly Ile
385                 390                 395                 400 acc ggt gat ttc agt gcc gag agc cag ttt gcc ggc aac ata gag atc       1248
Thr Gly Asp Phe Ser Ala Glu Ser Gln Phe Ala Gly Asn Ile Glu Ile
                405                 410                 415 ggt gct ccc gtg ccg ctc gcg gct gac agc cat tcc tcc aag ctg cag       1296
Gly Ala Pro Val Pro Leu Ala Ala Asp Ser His Ser Ser Lys Leu Gln
            420                 425                 430 agt gtg gac ggc gct ggt caa ggc ctg agg ctg gag atc ccg ctc gat       1344
Ser Val Asp Gly Ala Gly Gln Gly Leu Arg Leu Glu Ile Pro Leu Asp
        435                 440                 445 gcg caa gag ctc tcc ggg ctt ggc ttc aac aac gtc agc ctc agc gtg       1392
Ala Gln Glu Leu Ser Gly Leu Gly Phe Asn Asn Val Ser Leu Ser Val
    450                 455                 460 acc cct gct gcc aat caa                                               1410
Thr Pro Ala Ala Asn Gln
465                 470

<210> SEQ ID NO 4
<211> LENGTH: 470
<212> TYPE: PRT
<213> ORGANISM: Artificial Sequence
<220> FEATURE:
<223> OTHER INFORMATION: Proaerolysin with a PSA sequence substituted
      for the furin site.

<400> SEQUENCE: 4

Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125
```

```
Gly Gly Asn His Ser Gln Tyr Val Gly Glu Asp Met Asp Val Thr Arg
        130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Gly Trp Ala Val Asn Asp Ser
        195                 200                 205

Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Gln Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
        275                 280                 285

Ser Lys Ile Pro Val Lys Ile Glu Leu Tyr Lys Ala Asp Ile Ser Tyr
    290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala
            340                 345                 350

Ser Ser Ile Arg Tyr Gln Trp Asp Lys Arg Tyr Ile Pro Gly Glu Val
        355                 360                 365

Lys Trp Trp Asp Trp Asn Trp Thr Ile Gln Asn Gly Leu Ser Thr
    370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Leu Ala Ala Asp Ser His Ser Ser Lys Leu Gln
            420                 425                 430

Ser Val Asp Gly Ala Gly Gln Gly Leu Arg Leu Glu Ile Pro Leu Asp
        435                 440                 445

Ala Gln Glu Leu Ser Gly Leu Gly Phe Asn Asn Val Ser Leu Ser Val
    450                 455                 460

Thr Pro Ala Ala Asn Gln
465                 470

<210> SEQ ID NO 5
<211> LENGTH: 6
<212> TYPE: PRT
<213> ORGANISM: Homo Sapiens

<400> SEQUENCE: 5

His Ser Ser Lys Leu Gln
1               5

<210> SEQ ID NO 6
```

<211> LENGTH: 1410
<212> TYPE: DNA
<213> ORGANISM: Artificial Sequence
<220> FEATURE:
<223> OTHER INFORMATION: Proaerolysin with a PSA sequence substituted
      for the furin site
<220> FEATURE:
<221> NAME/KEY: CDS
<222> LOCATION: (1)..(1410)

<400> SEQUENCE: 6

```
gca gag ccc gtc tat cca gac cag ctt cgc ttg ttt tca ttg ggc caa      48
Ala Glu Pro Val Tyr Pro Asp Gln Leu Arg Leu Phe Ser Leu Gly Gln
1               5                   10                  15 ggg gtc tgt ggc gac aag tat cgc ccc gtc aat cga gaa gaa gcc caa      96
Gly Val Cys Gly Asp Lys Tyr Arg Pro Val Asn Arg Glu Glu Ala Gln
            20                  25                  30 agc gtt aaa agc aat att gtc ggc atg atg ggg caa tgg caa ata agc     144
Ser Val Lys Ser Asn Ile Val Gly Met Met Gly Gln Trp Gln Ile Ser
        35                  40                  45 ggg ctg gcc aac ggc tgg gtc att atg ggg ccg ggt tat aac ggt gaa     192
Gly Leu Ala Asn Gly Trp Val Ile Met Gly Pro Gly Tyr Asn Gly Glu
    50                  55                  60 ata aaa cca ggg aca gcg tcc aat acc tgg tgt tat ccg acc aat cct     240
Ile Lys Pro Gly Thr Ala Ser Asn Thr Trp Cys Tyr Pro Thr Asn Pro
65                  70                  75                  80 gtt acc ggt gaa ata ccg aca ctg tct gcc ctg gat att cca gat ggt     288
Val Thr Gly Glu Ile Pro Thr Leu Ser Ala Leu Asp Ile Pro Asp Gly
                85                  90                  95 gac gaa gtc gat gtg cag tgg cga ctg gta cat gac agt gcg aat ttc     336
Asp Glu Val Asp Val Gln Trp Arg Leu Val His Asp Ser Ala Asn Phe
            100                 105                 110 atc aaa cca acc agc tat ctg gcc cat tac ctc ggt tat gcc tgg gtg     384
Ile Lys Pro Thr Ser Tyr Leu Ala His Tyr Leu Gly Tyr Ala Trp Val
        115                 120                 125 ggc ggc aat cac agc caa tat gtc ggc gaa gac atg gat gtg acc cgt     432
Gly Gly Asn His Ser Gln Tyr Val Gly Glu Asp Met Asp Val Thr Arg
    130                 135                 140 gat ggc gac ggc tgg gtg atc cgt ggc aac aat gac ggc ggt tgt gac     480
Asp Gly Asp Gly Trp Val Ile Arg Gly Asn Asn Asp Gly Gly Cys Asp
145                 150                 155                 160 ggc tat cgc tgt ggt gac aag acg gcc atc aag gtc agc aac ttc gcc     528
Gly Tyr Arg Cys Gly Asp Lys Thr Ala Ile Lys Val Ser Asn Phe Ala
                165                 170                 175 tat aac ctg gat ccc gac agc ttc aag cat ggc gat gtc acc cag tcc     576
Tyr Asn Leu Asp Pro Asp Ser Phe Lys His Gly Asp Val Thr Gln Ser
            180                 185                 190 gac cgc cag ctg gtc aag act gtg gtg ggc tgg gcg gtc aac gac agc     624
Asp Arg Gln Leu Val Lys Thr Val Val Gly Trp Ala Val Asn Asp Ser
        195                 200                 205 gac acc ccc caa tcc ggc tat gac gtc acc ctg cgc tac gac aca gcc     672
Asp Thr Pro Gln Ser Gly Tyr Asp Val Thr Leu Arg Tyr Asp Thr Ala
    210                 215                 220 acc aac tgg tcc aag acc aac acc tat ggc ctg agc gag aag gtg acc     720
Thr Asn Trp Ser Lys Thr Asn Thr Tyr Gly Leu Ser Glu Lys Val Thr
225                 230                 235                 240 acc aag aac aag ttc aag tgg cca ctg gtg ggg gaa acc caa ctc tcc     768
Thr Lys Asn Lys Phe Lys Trp Pro Leu Val Gly Glu Thr Gln Leu Ser
                245                 250                 255 atc gag att gct gcc aat cag tcc tgg gcg tcc cag aac ggg ggc tcg     816
Ile Glu Ile Ala Ala Asn Gln Ser Trp Ala Ser Gln Asn Gly Gly Ser
            260                 265                 270
```

```
acc acc acc tcc ctg tct cag tcc gtg cga ccg act gtg ccg gcc cgc      864
Thr Thr Thr Ser Leu Ser Gln Ser Val Arg Pro Thr Val Pro Ala Arg
        275                 280                 285 tcc aag atc ccg gtg aag ata gag ctc tac aag gcc gac atc tcc tat      912
Ser Lys Ile Pro Val Lys Ile Glu Leu Tyr Lys Ala Asp Ile Ser Tyr
290                 295                 300 ccc tat gag ttc aag gcc gat gtc agc tat gac ctg acc ctg agc ggc      960
Pro Tyr Glu Phe Lys Ala Asp Val Ser Tyr Asp Leu Thr Leu Ser Gly
305                 310                 315                 320 ttc ctg cgc tgg ggc ggc aac gcc tgg tat acc cac ccg gac aac cgt     1008
Phe Leu Arg Trp Gly Gly Asn Ala Trp Tyr Thr His Pro Asp Asn Arg
                325                 330                 335 ccg aac tgg aac cac acc ttc gtc ata ggt ccg tac aag gac aag gcg     1056
Pro Asn Trp Asn His Thr Phe Val Ile Gly Pro Tyr Lys Asp Lys Ala
            340                 345                 350 agc agc att cgg tac cag tgg gac aag cgt tac atc ccg ggt gaa gtg     1104
Ser Ser Ile Arg Tyr Gln Trp Asp Lys Arg Tyr Ile Pro Gly Glu Val
        355                 360                 365 aag tgg tgg gac tgg aac tgg acc ata cag cag aac ggt ctg tct acc     1152
Lys Trp Trp Asp Trp Asn Trp Thr Ile Gln Gln Asn Gly Leu Ser Thr
370                 375                 380 atg cag aac aac ctg gcc aga gtg ctg cgc ccg gtg cgg gcg ggg atc     1200
Met Gln Asn Asn Leu Ala Arg Val Leu Arg Pro Val Arg Ala Gly Ile
385                 390                 395                 400 acc ggt gat ttc agt gcc gag agc cag ttt gcc ggc aac ata gag atc     1248
Thr Gly Asp Phe Ser Ala Glu Ser Gln Phe Ala Gly Asn Ile Glu Ile
                405                 410                 415 ggt gct ccc gtg ccg ctc gcg gct gac agc cat tcc tcc aag ctg cag     1296
Gly Ala Pro Val Pro Leu Ala Ala Asp Ser His Ser Ser Lys Leu Gln
            420                 425                 430 agt gcc gac ggc gct ggt caa ggc ctg agg ctg gag atc ccg ctc gat     1344
Ser Ala Asp Gly Ala Gly Gln Gly Leu Arg Leu Glu Ile Pro Leu Asp
        435                 440                 445 gcg caa gag ctc tcc ggg ctt ggc ttc aac aac gtc agc ctc agc gtg     1392
Ala Gln Glu Leu Ser Gly Leu Gly Phe Asn Asn Val Ser Leu Ser Val
450                 455                 460 acc cct gct gcc aat caa                                             1410
Thr Pro Ala Ala Asn Gln
465                 470

<210> SEQ ID NO 7
<211> LENGTH: 470
<212> TYPE: PRT
<213> ORGANISM: Artificial Sequence
<220> FEATURE:
<223> OTHER INFORMATION: Proaerolysin with a PSA sequence substituted
      for the furin site

<400> SEQUENCE: 7

Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Thr Ala Ser Asn Thr Trp Cys Tyr Pro Thr Asn Pro
65                  70                  75                  80
```

-continued

```
Val Thr Gly Glu Ile Pro Thr Leu Ser Ala Leu Asp Ile Pro Asp Gly
                 85                  90                  95
Asp Glu Val Asp Val Gln Trp Arg Leu Val His Asp Ser Ala Asn Phe
            100                 105                 110
Ile Lys Pro Thr Ser Tyr Leu Ala His Tyr Leu Gly Tyr Ala Trp Val
        115                 120                 125
Gly Gly Asn His Ser Gln Tyr Val Gly Glu Asp Met Asp Val Thr Arg
130                 135                 140
Asp Gly Asp Gly Trp Val Ile Arg Gly Asn Asn Asp Gly Gly Cys Asp
145                 150                 155                 160
Gly Tyr Arg Cys Gly Asp Lys Thr Ala Ile Lys Val Ser Asn Phe Ala
                165                 170                 175
Tyr Asn Leu Asp Pro Asp Ser Phe Lys His Gly Asp Val Thr Gln Ser
            180                 185                 190
Asp Arg Gln Leu Val Lys Thr Val Gly Trp Ala Val Asn Asp Ser
        195                 200                 205
Asp Thr Pro Gln Ser Gly Tyr Asp Val Thr Leu Arg Tyr Asp Thr Ala
    210                 215                 220
Thr Asn Trp Ser Lys Thr Asn Thr Tyr Gly Leu Ser Glu Lys Val Thr
225                 230                 235                 240
Thr Lys Asn Lys Phe Lys Trp Pro Leu Val Gly Glu Thr Gln Leu Ser
                245                 250                 255
Ile Glu Ile Ala Ala Asn Gln Ser Trp Ala Ser Gln Asn Gly Gly Ser
            260                 265                 270
Thr Thr Thr Ser Leu Ser Gln Ser Val Arg Pro Thr Val Pro Ala Arg
        275                 280                 285
Ser Lys Ile Pro Val Lys Ile Glu Leu Tyr Lys Ala Asp Ile Ser Tyr
    290                 295                 300
Pro Tyr Glu Phe Lys Ala Asp Val Ser Tyr Asp Leu Thr Leu Ser Gly
305                 310                 315                 320
Phe Leu Arg Trp Gly Gly Asn Ala Trp Tyr Thr His Pro Asp Asn Arg
                325                 330                 335
Pro Asn Trp Asn His Thr Phe Val Ile Gly Pro Tyr Lys Asp Lys Ala
            340                 345                 350
Ser Ser Ile Arg Tyr Gln Trp Asp Lys Arg Tyr Ile Pro Gly Glu Val
        355                 360                 365
Lys Trp Trp Asp Trp Asn Trp Thr Ile Gln Gln Asn Gly Leu Ser Thr
    370                 375                 380
Met Gln Asn Asn Leu Ala Arg Val Leu Arg Pro Val Arg Ala Gly Ile
385                 390                 395                 400
Thr Gly Asp Phe Ser Ala Glu Ser Gln Phe Ala Gly Asn Ile Glu Ile
                405                 410                 415
Gly Ala Pro Val Pro Leu Ala Ala Asp Ser His Ser Ser Lys Leu Gln
            420                 425                 430
Ser Ala Asp Gly Ala Gly Gln Gly Leu Arg Leu Glu Ile Pro Leu Asp
        435                 440                 445
Ala Gln Glu Leu Ser Gly Leu Gly Phe Asn Asn Val Ser Leu Ser Val
    450                 455                 460
Thr Pro Ala Ala Asn Gln
465                 470

<210> SEQ ID NO 8
<211> LENGTH: 8
<212> TYPE: PRT
```

<210> SEQ ID NO 9
<211> LENGTH: 1410
<212> TYPE: DNA
<213> ORGANISM: Artificial Sequence
<220> FEATURE:
<223> OTHER INFORMATION: PSA cleavage site

<400> SEQUENCE: 8

His Ser Ser Lys Leu Gln Ser Ala
1               5

<210> SEQ ID NO 9
<211> LENGTH: 1410
<212> TYPE: DNA
<213> ORGANISM: Artificial Sequence
<220> FEATURE:
<223> OTHER INFORMATION: Proaerolysin with a PSA sequence substituted
      for the furin site.
<220> FEATURE:
<221> NAME/KEY: CDS
<222> LOCATION: (1)..(1410)

<400> SEQUENCE: 9

```
gca gag ccc gtc tat cca gac cag ctt cgc ttg ttt tca ttg ggc caa       48
Ala Glu Pro Val Tyr Pro Asp Gln Leu Arg Leu Phe Ser Leu Gly Gln
1               5                   10                  15 ggg gtc tgt ggc gac aag tat cgc ccc gtc aat cga gaa gaa gcc caa       96
Gly Val Cys Gly Asp Lys Tyr Arg Pro Val Asn Arg Glu Glu Ala Gln
            20                  25                  30 agc gtt aaa agc aat att gtc ggc atg atg ggg caa tgg caa ata agc      144
Ser Val Lys Ser Asn Ile Val Gly Met Met Gly Gln Trp Gln Ile Ser
        35                  40                  45 ggg ctg gcc aac ggc tgg gtc att atg ggg ccg ggt tat aac ggt gaa      192
Gly Leu Ala Asn Gly Trp Val Ile Met Gly Pro Gly Tyr Asn Gly Glu
    50                  55                  60 ata aaa cca ggg aca gcg tcc aat acc tgg tgt tat ccg acc aat cct      240
Ile Lys Pro Gly Thr Ala Ser Asn Thr Trp Cys Tyr Pro Thr Asn Pro
65                  70                  75                  80 gtt acc ggt gaa ata ccg aca ctg tct gcc ctg gat att cca gat ggt      288
Val Thr Gly Glu Ile Pro Thr Leu Ser Ala Leu Asp Ile Pro Asp Gly
                85                  90                  95 gac gaa gtc gat gtg cag tgg cga ctg gta cat gac agt gcg aat ttc      336
Asp Glu Val Asp Val Gln Trp Arg Leu Val His Asp Ser Ala Asn Phe
            100                 105                 110 atc aaa cca acc agc tat ctg gcc cat tac ctc ggt tat gcc tgg gtg      384
Ile Lys Pro Thr Ser Tyr Leu Ala His Tyr Leu Gly Tyr Ala Trp Val
        115                 120                 125 ggc ggc aat cac agc caa tat gtc ggc gaa gac atg gat gtg acc cgt      432
Gly Gly Asn His Ser Gln Tyr Val Gly Glu Asp Met Asp Val Thr Arg
    130                 135                 140 gat ggc gac ggc tgg gtg atc cgt ggc aac aat gac ggc ggc tgt gac      480
Asp Gly Asp Gly Trp Val Ile Arg Gly Asn Asn Asp Gly Gly Cys Asp
145                 150                 155                 160 ggc tat cgc tgt ggt gac aag acg gcc atc aag gtc agc aac ttc gcc      528
Gly Tyr Arg Cys Gly Asp Lys Thr Ala Ile Lys Val Ser Asn Phe Ala
                165                 170                 175 tat aac ctg gat ccc gac agc ttc aag cat ggc gat gtc acc cag tcc      576
Tyr Asn Leu Asp Pro Asp Ser Phe Lys His Gly Asp Val Thr Gln Ser
            180                 185                 190 gac cgc cag ctg gtc aag act gtg gtg ggc tgg gcg gtc aac gac agc      624
Asp Arg Gln Leu Val Lys Thr Val Val Gly Trp Ala Val Asn Asp Ser
        195                 200                 205 gac acc ccc caa tcc ggc tat gac gtc acc ctg cgc tac gac aca gcc      672
Asp Thr Pro Gln Ser Gly Tyr Asp Val Thr Leu Arg Tyr Asp Thr Ala
    210                 215                 220
```

-continued

```
acc aac tgg tcc aag acc aac acc tat ggc ctg agc gag aag gtg acc      720
Thr Asn Trp Ser Lys Thr Asn Thr Tyr Gly Leu Ser Glu Lys Val Thr
225                 230                 235                 240 acc aag aac aag ttc aag tgg cca ctg gtg ggg gaa acc caa ctc tcc      768
Thr Lys Asn Lys Phe Lys Trp Pro Leu Val Gly Glu Thr Gln Leu Ser
                245                 250                 255 atc gag att gct gcc aat cag tcc tgg gcg tcc cag aac ggg ggc tcg      816
Ile Glu Ile Ala Ala Asn Gln Ser Trp Ala Ser Gln Asn Gly Gly Ser
            260                 265                 270 acc acc acc tcc ctg tct cag tcc gtg cga ccg act gtg ccg gcc cgc      864
Thr Thr Thr Ser Leu Ser Gln Ser Val Arg Pro Thr Val Pro Ala Arg
        275                 280                 285 tcc aag atc ccg gtg aag ata gag ctc tac aag gcc gac atc tcc tat      912
Ser Lys Ile Pro Val Lys Ile Glu Leu Tyr Lys Ala Asp Ile Ser Tyr
    290                 295                 300 ccc tat gag ttc aag gcc gat gtc agc tat gac ctg acc ctg agc ggc      960
Pro Tyr Glu Phe Lys Ala Asp Val Ser Tyr Asp Leu Thr Leu Ser Gly
305                 310                 315                 320 ttc ctg cgc tgg ggc ggc aac gcc tgg tat acc cac ccg gac aac cgt     1008
Phe Leu Arg Trp Gly Gly Asn Ala Trp Tyr Thr His Pro Asp Asn Arg
                325                 330                 335 ccg aac tgg aac cac acc ttc gtc ata ggt ccg tac aag gac aag gcg     1056
Pro Asn Trp Asn His Thr Phe Val Ile Gly Pro Tyr Lys Asp Lys Ala
            340                 345                 350 agc agc att cgg tac cag tgg gac aag cgt tac atc ccg ggt gaa gtg     1104
Ser Ser Ile Arg Tyr Gln Trp Asp Lys Arg Tyr Ile Pro Gly Glu Val
        355                 360                 365 aag tgg tgg gac tgg aac tgg acc ata cag cag aac ggt ctg tct acc     1152
Lys Trp Trp Asp Trp Asn Trp Thr Ile Gln Gln Asn Gly Leu Ser Thr
    370                 375                 380 atg cag aac aac ctg gcc aga gtg ctg cgc ccg gtg cgg gcg ggg atc     1200
Met Gln Asn Asn Leu Ala Arg Val Leu Arg Pro Val Arg Ala Gly Ile
385                 390                 395                 400 acc ggt gat ttc agt gcc gag agc cag ttt gcc ggc aac ata gag atc     1248
Thr Gly Asp Phe Ser Ala Glu Ser Gln Phe Ala Gly Asn Ile Glu Ile
                405                 410                 415 ggt gct ccc gtg ccg ctc gcg gct gac tcc cag ttc tat agc agc aat     1296
Gly Ala Pro Val Pro Leu Ala Ala Asp Ser Gln Phe Tyr Ser Ser Asn
            420                 425                 430 agt gtg gac ggc gct ggt caa ggc ctg agg ctg gag atc ccg ctc gat     1344
Ser Val Asp Gly Ala Gly Gln Gly Leu Arg Leu Glu Ile Pro Leu Asp
        435                 440                 445 gcg caa gag ctc tcc ggg ctt ggc ttc aac aac gtc agc ctc agc gtg     1392
Ala Gln Glu Leu Ser Gly Leu Gly Phe Asn Asn Val Ser Leu Ser Val
    450                 455                 460 acc cct gct gcc aat caa                                             1410
Thr Pro Ala Ala Asn Gln
465                 470

<210> SEQ ID NO 10
<211> LENGTH: 470
<212> TYPE: PRT
<213> ORGANISM: Artificial Sequence
<220> FEATURE:
<223> OTHER INFORMATION: Proaerolysin with a PSA sequence substituted
      for the furin site.

<400> SEQUENCE: 10

Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
```

-continued

```
                    20                  25                  30
Ser Val Lys Ser Asn Ile Val Gly Met Met Gly Gln Trp Gln Ile Ser
             35                  40                  45

Gly Leu Ala Asn Gly Trp Val Ile Met Gly Pro Gly Tyr Asn Gly Glu
         50                  55                  60

Ile Lys Pro Gly Thr Ala Ser Asn Thr Trp Cys Tyr Pro Thr Asn Pro
 65                  70                  75                  80

Val Thr Gly Glu Ile Pro Thr Leu Ser Ala Leu Asp Ile Pro Asp Gly
                 85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
            115                 120                 125

Gly Gly Asn His Ser Gln Tyr Val Gly Glu Asp Met Asp Val Thr Arg
            130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Gly Trp Ala Val Asn Asp Ser
            195                 200                 205

Asp Thr Pro Gln Ser Gly Tyr Asp Val Thr Leu Arg Tyr Asp Thr Ala
210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Gln Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
            275                 280                 285

Ser Lys Ile Pro Val Lys Ile Glu Leu Tyr Lys Ala Asp Ile Ser Tyr
            290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala
            340                 345                 350

Ser Ser Ile Arg Tyr Gln Trp Asp Lys Arg Tyr Ile Pro Gly Glu Val
            355                 360                 365

Lys Trp Trp Asp Trp Asn Trp Thr Ile Gln Gln Asn Gly Leu Ser Thr
            370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Leu Ala Ala Asp Ser Gln Phe Tyr Ser Ser Asn
            420                 425                 430

Ser Val Asp Gly Ala Gly Gln Gly Leu Arg Leu Glu Ile Pro Leu Asp
            435                 440                 445
```

```
Ala Gln Glu Leu Ser Gly Leu Gly Phe Asn Asn Val Ser Leu Ser Val
    450                 455                 460

Thr Pro Ala Ala Asn Gln
465                 470

<210> SEQ ID NO 11
<211> LENGTH: 6
<212> TYPE: PRT
<213> ORGANISM: Artificial Sequence
<220> FEATURE:
<223> OTHER INFORMATION: PSA cleavage site

<400> SEQUENCE: 11

Gln Phe Tyr Ser Ser Asn
1               5

<210> SEQ ID NO 12
<211> LENGTH: 1410
<212> TYPE: DNA
<213> ORGANISM: Artificial Sequence
<220> FEATURE:
<223> OTHER INFORMATION: Proaerolysin with a PSA sequence substituted
      for the furin site.
<220> FEATURE:
<221> NAME/KEY: CDS
<222> LOCATION: (1)..(1410)

<400> SEQUENCE: 12 gca gag ccc gtc tat cca gac cag ctt cgc ttg ttt tca ttg ggc caa      48
Ala Glu Pro Val Tyr Pro Asp Gln Leu Arg Leu Phe Ser Leu Gly Gln
1               5                   10                  15 ggg gtc tgt ggc gac aag tat cgc ccc gtc aat cga gaa gaa gcc caa      96
Gly Val Cys Gly Asp Lys Tyr Arg Pro Val Asn Arg Glu Glu Ala Gln
            20                  25                  30 agc gtt aaa agc aat att gtc ggc atg atg ggg caa tgg caa ata agc     144
Ser Val Lys Ser Asn Ile Val Gly Met Met Gly Gln Trp Gln Ile Ser
        35                  40                  45 ggg ctg gcc aac ggc tgg gtc att atg ggg ccg ggt tat aac ggt gaa     192
Gly Leu Ala Asn Gly Trp Val Ile Met Gly Pro Gly Tyr Asn Gly Glu
    50                  55                  60 ata aaa cca ggg aca gcg tcc aat acc tgg tgt tat ccg acc aat cct     240
Ile Lys Pro Gly Thr Ala Ser Asn Thr Trp Cys Tyr Pro Thr Asn Pro
65                  70                  75                  80 gtt acc ggt gaa ata ccg aca ctg tct gcc ctg gat att cca gat ggt     288
Val Thr Gly Glu Ile Pro Thr Leu Ser Ala Leu Asp Ile Pro Asp Gly
                85                  90                  95 gac gaa gtc gat gtg cag tgg cga ctg gta cat gac agt gcg aat ttc     336
Asp Glu Val Asp Val Gln Trp Arg Leu Val His Asp Ser Ala Asn Phe
            100                 105                 110 atc aaa cca acc agc tat ctg gcc cat tac ctc ggt tat gcc tgg gtg     384
Ile Lys Pro Thr Ser Tyr Leu Ala His Tyr Leu Gly Tyr Ala Trp Val
        115                 120                 125 ggc ggc aat cac agc caa tat gtc ggc gaa gac atg gat gtg acc cgt     432
Gly Gly Asn His Ser Gln Tyr Val Gly Glu Asp Met Asp Val Thr Arg
    130                 135                 140 gat ggc gac ggc tgg gtg atc cgt ggc aac aat gac ggc ggt tgt gac     480
Asp Gly Asp Gly Trp Val Ile Arg Gly Asn Asn Asp Gly Gly Cys Asp
145                 150                 155                 160 ggc tat cgc tgt ggt gac aag acg gcc atc aag gtc agc aac ttc gcc     528
Gly Tyr Arg Cys Gly Asp Lys Thr Ala Ile Lys Val Ser Asn Phe Ala
                165                 170                 175 tat aac ctg gat ccc gac agc ttc aag cat ggc gat gtc acc cag tcc     576
```

```
                Tyr Asn Leu Asp Pro Asp Ser Phe Lys His Gly Asp Val Thr Gln Ser
                            180                 185                 190 gac cgc cag ctg gtc aag act gtg gtg ggc tgg gcg gtc aac gac agc       624
Asp Arg Gln Leu Val Lys Thr Val Val Gly Trp Ala Val Asn Asp Ser
            195                 200                 205 gac acc ccc caa tcc ggc tat gac gtc acc ctg cgc tac gac aca gcc       672
Asp Thr Pro Gln Ser Gly Tyr Asp Val Thr Leu Arg Tyr Asp Thr Ala
        210                 215                 220 acc aac tgg tcc aag acc aac acc tat ggc ctg agc gag aag gtg acc       720
Thr Asn Trp Ser Lys Thr Asn Thr Tyr Gly Leu Ser Glu Lys Val Thr
225                 230                 235                 240 acc aag aac aag ttc aag tgg cca ctg gtg ggg gaa acc caa ctc tcc       768
Thr Lys Asn Lys Phe Lys Trp Pro Leu Val Gly Glu Thr Gln Leu Ser
                245                 250                 255 atc gag att gct gcc aat cag tcc tgg gcg tcc cag aac ggg ggc tcg       816
Ile Glu Ile Ala Ala Asn Gln Ser Trp Ala Ser Gln Asn Gly Gly Ser
            260                 265                 270 acc acc acc tcc ctg tct cag tcc gtg cga ccg act gtg ccg gcc cgc       864
Thr Thr Thr Ser Leu Ser Gln Ser Val Arg Pro Thr Val Pro Ala Arg
        275                 280                 285 tcc aag atc ccg gtg aag ata gag ctc tac aag gcc gac atc tcc tat       912
Ser Lys Ile Pro Val Lys Ile Glu Leu Tyr Lys Ala Asp Ile Ser Tyr
    290                 295                 300 ccc tat gag ttc aag gcc gat gtc agc tat gac ctg acc ctg agc ggc       960
Pro Tyr Glu Phe Lys Ala Asp Val Ser Tyr Asp Leu Thr Leu Ser Gly
305                 310                 315                 320 ttc ctg cgc tgg ggc ggc aac gcc tgg tat acc cac ccg gac aac cgt      1008
Phe Leu Arg Trp Gly Gly Asn Ala Trp Tyr Thr His Pro Asp Asn Arg
                325                 330                 335 ccg aac tgg aac cac acc ttc gtc ata ggt ccg tac aag gac aag gcg      1056
Pro Asn Trp Asn His Thr Phe Val Ile Gly Pro Tyr Lys Asp Lys Ala
            340                 345                 350 agc agc att cgg tac cag tgg gac aag cgt tac atc ccg ggt gaa gtg      1104
Ser Ser Ile Arg Tyr Gln Trp Asp Lys Arg Tyr Ile Pro Gly Glu Val
        355                 360                 365 aag tgg tgg gac tgg aac tgg acc ata cag cag aac ggt ctg tct acc      1152
Lys Trp Trp Asp Trp Asn Trp Thr Ile Gln Gln Asn Gly Leu Ser Thr
    370                 375                 380 atg cag aac aac ctg gcc aga gtg ctg cgc ccg gtg cgg gcg ggg atc      1200
Met Gln Asn Asn Leu Ala Arg Val Leu Arg Pro Val Arg Ala Gly Ile
385                 390                 395                 400 acc ggt gat ttc agt gcc gag agc cag ttt gcc ggc aac ata gag atc      1248
Thr Gly Asp Phe Ser Ala Glu Ser Gln Phe Ala Gly Asn Ile Glu Ile
                405                 410                 415 ggt gct ccc gtg ccg ctc gcg gct gac ggt ata agt agt ttc cag agt      1296
Gly Ala Pro Val Pro Leu Ala Ala Asp Gly Ile Ser Ser Phe Gln Ser
            420                 425                 430 agt gtg gac ggc gct ggt caa ggc ctg agg ctg gag atc ccg ctc gat      1344
Ser Val Asp Gly Ala Gly Gln Gly Leu Arg Leu Glu Ile Pro Leu Asp
        435                 440                 445 gcg caa gag ctc tcc ggg ctt ggc ttc aac aac gtc agc ctc agc gtg      1392
Ala Gln Glu Leu Ser Gly Leu Gly Phe Asn Asn Val Ser Leu Ser Val
    450                 455                 460 acc cct gct gcc aat caa                                              1410
Thr Pro Ala Ala Asn Gln
465                 470

<210> SEQ ID NO 13
<211> LENGTH: 470
<212> TYPE: PRT
```

<213> ORGANISM: Artificial Sequence
<220> FEATURE:
<223> OTHER INFORMATION: Proaerolysin with a PSA sequence substituted for the furin site.

<400> SEQUENCE: 13

```
Ala Glu Pro Val Tyr Pro Asp Gln Leu Arg Leu Phe Ser Leu Gly Gln
1               5                   10                  15
Gly Val Cys Gly Asp Lys Tyr Arg Pro Val Asn Arg Glu Glu Ala Gln
            20                  25                  30
Ser Val Lys Ser Asn Ile Val Gly Met Met Gly Gln Trp Gln Ile Ser
        35                  40                  45
Gly Leu Ala Asn Gly Trp Val Ile Met Gly Pro Gly Tyr Asn Gly Glu
    50                  55                  60
Ile Lys Pro Gly Thr Ala Ser Asn Thr Trp Cys Tyr Pro Thr Asn Pro
65                  70                  75                  80
Val Thr Gly Glu Ile Pro Thr Leu Ser Ala Leu Asp Ile Pro Asp Gly
                85                  90                  95
Asp Glu Val Asp Val Gln Trp Arg Leu Val His Asp Ser Ala Asn Phe
            100                 105                 110
Ile Lys Pro Thr Ser Tyr Leu Ala His Tyr Leu Gly Tyr Ala Trp Val
        115                 120                 125
Gly Gly Asn His Ser Gln Tyr Val Gly Glu Asp Met Asp Val Thr Arg
    130                 135                 140
Asp Gly Asp Gly Trp Val Ile Arg Gly Asn Asn Asp Gly Gly Cys Asp
145                 150                 155                 160
Gly Tyr Arg Cys Gly Asp Lys Thr Ala Ile Lys Val Ser Asn Phe Ala
                165                 170                 175
Tyr Asn Leu Asp Pro Asp Ser Phe Lys His Gly Asp Val Thr Gln Ser
            180                 185                 190
Asp Arg Gln Leu Val Lys Thr Val Val Gly Trp Ala Val Asn Asp Ser
        195                 200                 205
Asp Thr Pro Gln Ser Gly Tyr Asp Val Thr Leu Arg Tyr Asp Thr Ala
    210                 215                 220
Thr Asn Trp Ser Lys Thr Asn Thr Tyr Gly Leu Ser Glu Lys Val Thr
225                 230                 235                 240
Thr Lys Asn Lys Phe Lys Trp Pro Leu Val Gly Glu Thr Gln Leu Ser
                245                 250                 255
Ile Glu Ile Ala Ala Asn Gln Ser Trp Ala Ser Gln Asn Gly Gly Ser
            260                 265                 270
Thr Thr Thr Ser Leu Ser Gln Ser Val Arg Pro Thr Val Pro Ala Arg
        275                 280                 285
Ser Lys Ile Pro Val Lys Ile Glu Leu Tyr Lys Ala Asp Ile Ser Tyr
    290                 295                 300
Pro Tyr Glu Phe Lys Ala Asp Val Ser Tyr Asp Leu Thr Leu Ser Gly
305                 310                 315                 320
Phe Leu Arg Trp Gly Gly Asn Ala Trp Tyr Thr His Pro Asp Asn Arg
                325                 330                 335
Pro Asn Trp Asn His Thr Phe Val Ile Gly Pro Tyr Lys Asp Lys Ala
            340                 345                 350
Ser Ser Ile Arg Tyr Gln Trp Asp Lys Arg Tyr Ile Pro Gly Glu Val
        355                 360                 365
Lys Trp Trp Asp Trp Asn Trp Thr Ile Gln Gln Asn Gly Leu Ser Thr
    370                 375                 380
```

-continued

```
Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
            405                 410                 415

Gly Ala Pro Val Pro Leu Ala Ala Asp Gly Ile Ser Ser Phe Gln Ser
                420                 425                 430

Ser Val Asp Gly Ala Gly Gln Gly Leu Arg Leu Glu Ile Pro Leu Asp
            435                 440                 445

Ala Gln Glu Leu Ser Gly Leu Gly Phe Asn Asn Val Ser Leu Ser Val
        450                 455                 460

Thr Pro Ala Ala Asn Gln
465                 470

<210> SEQ ID NO 14
<211> LENGTH: 7
<212> TYPE: PRT
<213> ORGANISM: Artificial Sequence
<220> FEATURE:
<223> OTHER INFORMATION: PSA cleavage site

<400> SEQUENCE: 14

Gly Ile Ser Ser Phe Gln Ser
1               5

<210> SEQ ID NO 15
<211> LENGTH: 7
<212> TYPE: PRT
<213> ORGANISM: Homo sapiens

<400> SEQUENCE: 15

Lys Gly Ile Ser Ser Gln Tyr
1               5

<210> SEQ ID NO 16
<211> LENGTH: 7
<212> TYPE: PRT
<213> ORGANISM: Homo sapiens

<400> SEQUENCE: 16

Ser Arg Lys Ser Gln Gln Tyr
1               5

<210> SEQ ID NO 17
<211> LENGTH: 7
<212> TYPE: PRT
<213> ORGANISM: Homo sapiens

<400> SEQUENCE: 17

Ala Thr Lys Ser Lys Gln His
1               5

<210> SEQ ID NO 18
<211> LENGTH: 7
<212> TYPE: PRT
<213> ORGANISM: Homo sapiens

<400> SEQUENCE: 18

Lys Gly Leu Ser Ser Gln Cys
1               5

<210> SEQ ID NO 19
<211> LENGTH: 7
<212> TYPE: PRT
```

```
<213> ORGANISM: Homo sapiens

<400> SEQUENCE: 19

Leu Gly Gly Ser Ser Gln Leu
1 5

<210> SEQ ID NO 20
<211> LENGTH: 7
<212> TYPE: PRT
<213> ORGANISM: Homo sapiens

<400> SEQUENCE: 20

Glu His Ser Ser Lys Leu Gln
1 5

<210> SEQ ID NO 21
<211> LENGTH: 4
<212> TYPE: PRT
<213> ORGANISM: Homo sapiens

<400> SEQUENCE: 21

Ser Lys Leu Gln
1

<210> SEQ ID NO 22
<211> LENGTH: 10
<212> TYPE: PRT
<213> ORGANISM: Homo sapiens

<400> SEQUENCE: 22

Gln His Trp Ser Tyr Gly Leu Arg Pro Gly
1 5 10

<210> SEQ ID NO 23
<211> LENGTH: 10
<212> TYPE: PRT
<213> ORGANISM: Artificial Sequence
<220> FEATURE:
<223> OTHER INFORMATION: LHRH variant sequence.
<220> FEATURE:
<221> NAME/KEY: MISC_FEATURE
<222> LOCATION: (1)..(1)
<223> OTHER INFORMATION: Glu is a pyroglutamate
<220> FEATURE:
<221> NAME/KEY: MISC_FEATURE
<222> LOCATION: (6)..(6)
<223> OTHER INFORMATION: Lys is a D-Lys

<400> SEQUENCE: 23

Glu His Trp Ser Tyr Lys Leu Arg Pro Gly
1 5 10

<210> SEQ ID NO 24
<211> LENGTH: 397
<212> TYPE: PRT
<213> ORGANISM: Artificial Sequence
<220> FEATURE:
<223> OTHER INFORMATION: Variant proaerolysin peptide.
<220> FEATURE:
<221> NAME/KEY: MISC_FEATURE
<222> LOCATION: (1)..(1)
<223> OTHER INFORMATION: pyroglutamate
<220> FEATURE:
<221> NAME/KEY: MISC_FEATURE
<222> LOCATION: (6)..(6)
<223> OTHER INFORMATION: D-Lys

<400> SEQUENCE: 24

```
Glu His Trp Ser Tyr Lys Leu Arg Pro Gly Glu Ile Pro Thr Leu Ser
1               5                   10                  15

Ala Leu Asp Ile Pro Asp Gly Asp Glu Val Asp Val Gln Trp Arg Leu
            20                  25                  30

Val His Asp Ser Ala Asn Phe Ile Lys Pro Thr Ser Tyr Leu Ala His
        35                  40                  45

Tyr Leu Gly Tyr Ala Trp Val Gly Gly Asn His Ser Gln Tyr Val Gly
    50                  55                  60

Glu Asp Met Asp Val Thr Arg Asp Gly Asp Trp Val Ile Arg Gly
65                  70                  75                  80

Asn Asn Asp Gly Gly Cys Asp Gly Tyr Arg Cys Gly Asp Lys Thr Ala
                85                  90                  95

Ile Lys Val Ser Asn Phe Ala Tyr Asn Leu Asp Pro Asp Ser Phe Lys
            100                 105                 110

His Gly Asp Val Thr Gln Ser Asp Arg Gln Leu Val Lys Thr Val Val
        115                 120                 125

Gly Trp Ala Val Asn Asp Ser Asp Thr Pro Gln Ser Gly Tyr Asp Val
    130                 135                 140

Thr Leu Arg Tyr Asp Thr Ala Thr Asn Trp Ser Lys Thr Asn Thr Tyr
145                 150                 155                 160

Gly Leu Ser Glu Lys Val Thr Thr Lys Asn Lys Phe Lys Trp Pro Leu
                165                 170                 175

Val Gly Glu Thr Gln Leu Ser Ile Glu Ile Ala Ala Asn Gln Ser Trp
            180                 185                 190

Ala Ser Gln Asn Gly Gly Ser Thr Thr Thr Ser Leu Ser Gln Ser Val
        195                 200                 205

Arg Pro Thr Val Pro Ala Arg Ser Lys Ile Pro Val Lys Ile Glu Leu
    210                 215                 220

Tyr Lys Ala Asp Ile Ser Tyr Pro Tyr Glu Phe Lys Ala Asp Val Ser
225                 230                 235                 240

Tyr Asp Leu Thr Leu Ser Gly Phe Leu Arg Trp Gly Gly Asn Ala Trp
                245                 250                 255

Tyr Thr His Pro Asp Asn Arg Pro Asn Trp Asn His Thr Phe Val Ile
            260                 265                 270

Gly Pro Tyr Lys Asp Lys Ala Ser Ser Ile Arg Tyr Gln Trp Asp Lys
        275                 280                 285

Arg Tyr Ile Pro Gly Glu Val Lys Trp Trp Asp Trp Asn Trp Thr Ile
    290                 295                 300

Gln Gln Asn Gly Leu Ser Thr Met Gln Asn Asn Leu Ala Arg Val Leu
305                 310                 315                 320

Arg Pro Val Arg Ala Gly Ile Thr Gly Asp Phe Ser Ala Glu Ser Gln
                325                 330                 335

Phe Ala Gly Asn Ile Glu Ile Gly Ala Pro Val Pro Leu Ala Ala Asp
            340                 345                 350

Ser His Ser Ser Lys Leu Gln Ser Val Asp Gly Ala Gln Gly Leu
        355                 360                 365

Arg Leu Glu Ile Pro Leu Asp Ala Gln Glu Leu Ser Gly Leu Gly Phe
    370                 375                 380

Asn Asn Val Ser Leu Ser Val Thr Pro Ala Ala Asn Gln
385                 390                 395

<210> SEQ ID NO 25
<211> LENGTH: 397
<212> TYPE: PRT
```

-continued

```
<213> ORGANISM: Artificial Sequence
<220> FEATURE:
<223> OTHER INFORMATION: Variant proaerolysin peptide.
<220> FEATURE:

```
                    -continued

Ser Lys Val Arg Arg Ala Arg Ser Val Asp Gly Ala Gly Gln Gly Leu
        355                 360                 365

Arg Leu Glu Ile Pro Leu Asp Ala Gln Glu Leu Ser Gly Leu Gly Phe
    370                 375                 380

Asn Asn Val Ser Leu Ser Val Thr Pro Ala Ala Asn Gln
385                 390                 395
```

PROAEROLYSIN CONTAINING PROTEASE ACTIVATION SEQUENCES AND METHODS OF USE FOR TREATMENT OF PROSTATE CANCER

CROSS REFERENCE TO RELATED APPLICATIONS

This application is a divisional of U.S. application Ser. No. 10/487,115 filed Feb. 18, 2004 (U.S. Pat. No. 7,282,476), which is the U.S. National Stage of International Application No. PCT/US02/27061, filed Aug. 23, 2002 (published in English under PCT Article 21(2)), which in turn claims the benefit of priority to U.S. Provisional Application No. 60/314,613, filed Aug. 24, 2001, both applications herein incorporated by reference in their entirety.

FIELD

This application relates to novel variant proaerolysin (PA) proteins and methods of their use to treat localized and metastatic prostate cancer.

BACKGROUND

One of every three cancers diagnosed in American males is of prostatic origin, making prostate cancer the most commonly diagnosed malignancy in males in the United States (Berges et al. *Clin. Cancer Res.* 1:473-480, 1995). The incidence of prostate cancer in the U.S. has not been decreased by changes in lifestyle; in fact, the incidence rate of clinical prostate cancer has increased steadily since the 1930's (Pinski et al. *Cancer Res.* 61:6372-6, 2001). Prostate cancer incidence increases with age more rapidly than any other type of cancer; less than 1% of prostate cancers are diagnosed in men less than 50 years of age (Furuya et al. *Cancer Res.* 54:6167-75, 1994). Thus, as the life expectancy of the male population increases over time, the incidence of clinical prostate cancer will also increase (Furuya et al. *Cancer Res.* 54:6167-75, 1994).

Currently there is no treatment that significantly prolongs survival in men with metastatic prostate cancer (Khan and Denmeade. *Prostate* 45:80-83, 2000). Medical castration with oral estrogen (androgen ablation) was the first effective systemic therapy for cancer, and remains the most generally useful prostate cancer therapy. Although androgen ablation therapy has a substantial palliative benefit, it has little impact on overall survival (Berges et al. *Clin. Cancer Res.* 1:473-480, 1995). This therapy eventually fails because the metastatic prostate cancer within an individual patient is heterogeneously composed of androgen-dependent and androgen-independent cancer cells (Christensen et al. *Bioorg. Medicinal Chem.* 7:1273-80, 1999). Following androgen ablation, androgen-dependent cells within these tumors stop proliferating and activate a cellular suicide pathway termed programmed cell death (PCD) or apoptosis. Because of the elimination of this subgroup of androgen-dependent cells, the majority of men with metastatic prostate cancers have a beneficial response to androgen-deprivation therapy. However, all patients eventually relapse to a state unresponsive to further anti-androgen therapy, no matter how completely given, due to the presence of androgen-independent prostate cancer cells within the metastatic sites. Unfortunately, the disease is uniformly fatal at this point because currently there is no therapy that effectively eliminates androgen-independent prostate cancer cells (Khan and Denmeade. *Prostate* 45:80-83, 2000).

Several alternative approaches to the treatment of prostate cancer have been proposed. One has been to develop methods to aggressively screen for local disease while it is still in the prostate and thus potentially treatable by definitive local therapy. Localized cancers are often moderately differentiated and smaller in volume. During the last several decades, there have been improvements to the surgical and radiotherapeutic management of localized prostate cancer. These improvements have culminated over the last several years in the death rate of prostate cancer decreasing for the first time in fifty years.

However, while this advance increased the cure rate, there are still a large number of men who are not cured by local therapies and eventually die from metastatic disease. This clinical reality has led to the development of non-hormonal treatments for metastatic prostate cancer. Standard anti-proliferative chemotherapeutic agents have not been successful as treatment for prostate cancer. These types of agents may be ineffective against androgen-independent prostatic cancers because these cancers have a remarkably low rate of proliferation when compared to other tumor types and many normal tissues such as skin, gastrointestinal tract and bone marrow. For example, the growth fraction in 117 metastatic sites of prostate cancer obtained from 11 androgen ablation failing patients at "warm" autopsy was 7.1±0.8%. (Pinski et al. *Cancer Res.* 61:6372-6, 2001). This low proliferative rate may explain the relative unresponsiveness of prostate cancer cells in humans to standard anti-proliferative chemotherapy, while highly proliferative androgen independent prostate cancer cell lines remain exquisitely sensitive to PCD induction in vitro.

Several strategies have been proposed for treatment of slowly-proliferating prostate cancers. One approach is to identify specific signaling pathways to which prostate cancer cells, during malignant transformation, acquire a unique dependence for survival. Once identified, small molecule or biological inhibitors of these pathways can be developed as therapeutics. An example of this approach is the use of small molecule or monoclonal antibody inhibitors of the Her2/neu or EGF receptor pathways. Another method is to inhibit a ubiquitous intracellular protein whose function is mandatory for survival of all cell types. This approach would overcome the problem of heterogeneity and "resistance" as all cancer cells within a tumor could be killed via this approach. However, the cytotoxicity would not be cell-type specific and administration of such a general toxin would be associated with significant systemic toxicity. Therefore, there is a need for a method for targeting cytotoxins directly to sites of prostate cancer.

Another strategy for treatment of slowly proliferating prostate cancers is to deliver cytotoxins that kill cells not through induction of apoptosis following inhibition of critical signaling or metabolic pathways but rather through non-specific cytolysis via disruption of the plasma membrane. Many cytolytic toxins have been described (Lesieur et al. *Mol. Membr. Biol.* 14:45064, 1997). These cytolytic toxins are often of bacterial origin, and, in general, are beta-sheet proteins that oligomerize in the plasma membrane to produce well-characterized pores that, once formed, lead to rapid cytolytic cell death (Rossjohn et al. *J. Struct. Biol.* 121:92-100, 1998). These toxins are also non-specific in their ability to kill cells, and therefore can not be administered as therapy without significant toxicity. Therefore, there is a need for agents to treat prostate cancer, which are predominantly cytotoxic to prostate cancer cells.

SUMMARY

Disclosed herein are variant proaerolysin (PA) molecules and methods of their use for treatment of localized and metastatic prostate cancers, such as slowly-proliferating prostate cancers.

In one example, a variant PA molecule includes a prostate-specific protease cleavage site, such as a prostate-specific antigen (PSA)-, prostate specific membrane antigen (PSMA)-, or human glandular kallikrein 2 (HK2)-specific cleavage site that functionally replaces the native PA furin cleavage site. In this way, administration of the disclosed variant PA molecules to a subject having prostate cancer results in activation of the disclosed variant PA molecules in the presence of the prostate-specific protease, and lysis of the cells, such as prostate cancer cells. In some examples, variant PA molecules also include a prostate tissue specific binding domain, to enhance targeting to cancer cells.

In another example, a variant PA molecule includes a furin cleavage site, and a prostate tissue specific binding domain which functionally replaces the native PA binding domain, to assist in targeting to prostate cancer cells.

Methods are disclosed for treatment of localized and metastatic prostate cancers using the disclosed variant PA molecules. In addition, methods are disclosed for stimulating a subject's immune system to enhance treatment of localized and metastatic prostate cancer.

BRIEF DESCRIPTION OF THE FIGURES

FIG. 1 is a schematic of proaerolysin domains (not drawn to scale) and shows the result of activation by furin.

FIG. 2 is a bar graph showing the results of a hemolysis assay in which PSA-PA1 is preincubated with human plasma or human plasma spiked with enzymatically active PSA (10, 000 ng/ml).

FIGS. 5A-5M are schematic drawings (not to scale) showing how a proaerolysin sequence can be altered to generate several different variant PA molecules. The "*" symbol represents one or more point mutations, and/or one or more deletions which decrease PA binding domain function (i.e. the ability to concentrate in a cell membrane).

SEQUENCE LISTING

Figure 3:
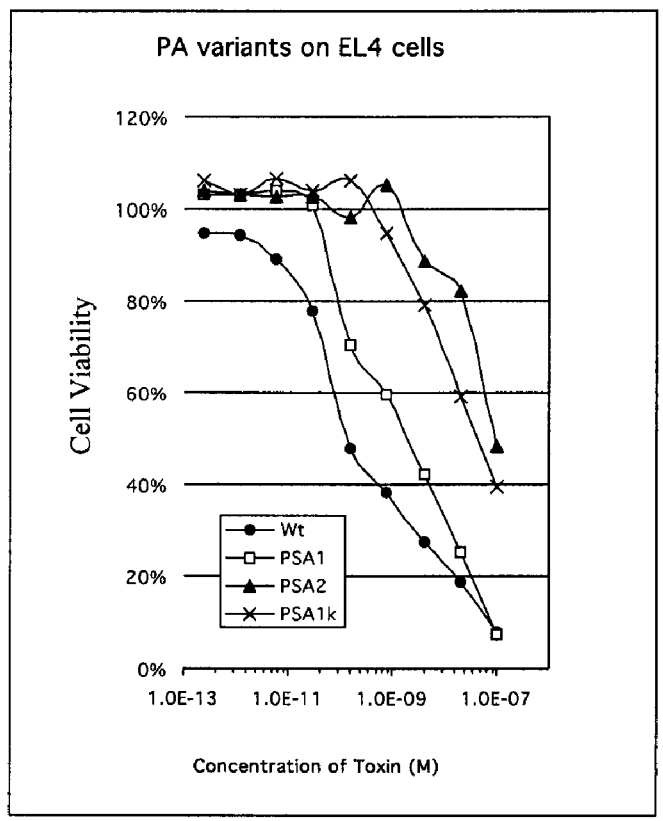
FIG. 3 is a graph comparing the in vitro toxicity of several proaerolysin variants which include a PSA cleavage site in place of the native furin site, to wild-type proaerolysin.

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NOS: 1 and 2 show a wild-type proaerolysin cDNA and protein sequence, respectively.

SEQ ID NOS: 3 and 4 show the PSA-PA1 cDNA and protein sequence, respectively, wherein the furin site of proaerolysin has been replaced with a PSA cleavage site.

SEQ ID NOS: 5 and 15-21 are PSA cleavage sites found in human semenogelin I and II proteins.

SEQ ID NOS: 6 and 7 show the PSA-1K cDNA and protein sequence, respectively, wherein the furin site of proaerolysin has been replaced with a PSA cleavage site.

SEQ ID NO: 8, 11, and 14-21 are alternative PSA cleavage sites.

SEQ ID NOS: 9 and 10 show the PSA-PA2 cDNA and protein sequence, respectively, wherein the furin site of proaerolysin has been replaced with a PSA cleavage site.

SEQ ID NOS: 12 and 13 show the PSA-PA3 cDNA and protein sequence, respectively, wherein the furin site of proaerolysin has been replaced with a PSA cleavage site.

SEQ ID NO: 22 is a native luteinizing hormone releasing hormone (LHRH) protein sequence.

SEQ ID NO: 23 is a modified LHRH protein sequence.

SEQ ID NO: 24 is a protein sequence of a variant PA peptide, wherein the furin site of PA has been replaced with a PSA cleavage site, and wherein the native binding domain of PA is deleted and replaced with SEQ ID NO: 23.

SEQ ID NO: 25 is a protein sequence of a variant PA peptide, wherein the furin site of PA is retained, and the native binding domain of PA has been deleted and replaced with SEQ ID NO: 23.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. As used herein and in the appended claims, the singular forms "a" or "an" or "the" include plural references unless the context clearly dictates otherwise. For example, reference to "a variant PA molecule" includes a plurality of such molecules and reference to "the antibody" includes reference to one or more antibodies and equivalents thereof known to those skilled in the art, and so forth.

Unless explained otherwise, all technical and scientific terms used herein have the same meaning as commonly understood to one of ordinary skill in the art to which this disclosure belongs.

Aerolysin: A channel-forming toxin produced as an inactive protoxin called proaerolysin (PA) (wild-type PA is shown in SEQ ID NOS: 1 and 2). The PA protein contains many discrete functionalities that include a binding domain (approximately amino acids 1-83 of SEQ ID NO: 2), a toxin domain (approximately amino acids 84-426 of SEQ ID NO: 2), and a C-terminal inhibitory peptide domain (approximately amino acids 427-470 of SEQ ID NO: 2) that contains a protease activation site (amino acids 427-432 of SEQ ID NO: 2).

The binding domain recognizes and binds to glycophosphatidylinositol (GPI) membrane anchors, such as are found in Thy-1 on T lymphocytes, the PIGA gene product found in erythrocyte membranes and Prostate Stem Cell Antigen (PSCA). Most mammalian cells express GPI anchored proteins on their surfaces. The activation or proteolysis site within proaerolysin is a six amino acid sequence that is recognized as a proteolytic substrate by the furin family of proteases. PA is activated upon hydrolysis of a C-terminal inhibitory segment by furin (FIG. 1). Activated aerolysin binds to GPI-anchored proteins in the cell membrane and forms a heptamer that inserts into the membrane producing well-defined channels of ~17 Å. Channel formation leads to rapid cell death via necrosis. Wild-type aerolysin is toxic to mammalian cells, including erythrocytes, for example at 1 nanomolar or less.

Animal: Living multicellular vertebrate organisms, a category which includes, for example, mammals and birds.

Antibody: Immunoglobulin molecules and immunologically active portions of immunoglobulin molecules, i.e., molecules that contain an antigen binding site which specifically binds (immunoreacts with) an antigen.

A naturally occurring antibody (e.g., IgG) includes four polypeptide chains, two heavy (H) chains and two light (L) chains inter-connected by disulfide bonds. However, the antigen-binding function of an antibody can be performed by fragments of a naturally occurring antibody. Thus, these antigen-binding fragments are also intended to be designated by the term antibody. Examples of binding fragments encompassed within the term antibody include (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., Nature 341:544-6, 1989) which consists of a VH domain; (v) an isolated complimentarity determining region (CDR); and (vi) an F(ab')2 fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv); Bird et al. *Science* 242: 423-6, 1988; and Huston et al., *Proc. Natl. Acad. Sci.* 85:5879-83, 1988) by recombinant methods. Such single chain antibodies are also included. In one embodiment, an antibody includes camelized antibodies (for example see Tanha et al., *J. Biol. Chem.* 276:24774-80, 2001).

In one example, antibody fragments are capable of crosslinking their target antigen, e.g., bivalent fragments such as F(ab')2 fragments. Alternatively, an antibody fragment which does not itself crosslink its target antigen (e.g., a Fab fragment) can be used in conjunction with a secondary antibody which serves to crosslink the antibody fragment, thereby crosslinking the target antigen. Antibodies can be fragmented using conventional techniques and the fragments screened for utility in the same manner as described for whole antibodies. An antibody is further intended to include bispecific and chimeric molecules that specifically bind the target antigen.

"Specifically binds" refers to the ability of individual antibodies to specifically immunoreact with an antigen. The binding is a non-random binding reaction between an antibody molecule and an antigenic determinant of the T cell surface molecule. The desired binding specificity is typically determined from the reference point of the ability of the antibody to differentially bind the T cell surface molecule and an unrelated antigen, and therefore distinguish between two different antigens, particularly where the two antigens have unique epitopes. An antibody that specifically binds to a particular epitope is referred to as a "specific antibody".

Cancer: Malignant neoplasm that has undergone characteristic anaplasia with loss of differentiation, increase rate of growth, invasion of surrounding tissue, and is capable of metastasis.

cDNA (complementary DNA): A piece of DNA lacking internal, non-coding segments (introns) and regulatory sequences which determine transcription. cDNA can be synthesized in the laboratory by reverse transcription from messenger RNA extracted from cells.

Chemical synthesis: An artificial means by which one can make a protein or peptide. A synthetic protein or peptide is one made by such artificial means.

Chemotherapy: In cancer treatment, chemotherapy refers to the administration of one or a combination of compounds to kill or slow the reproduction of rapidly multiplying cells. Chemotherapeutic agents include those known by those skilled in the art, including, but not limited to: 5-fluorouracil (5-FU), azathioprine, cyclophosphamide, antimetabolites (such as Fludarabine), antineoplastics (such as Etoposide, Doxorubicin, methotrexate, and Vincristine), carboplatin, cis-platinum and the taxanes, such as taxol and taxotere. Such agents can be co-administered with the disclosed variant PA molecules to a subject. Alternatively or in addition, chemotherapeutic agents can be administered prior to and/or subsequent to administration of the disclosed variant PA molecules to a subject. In one example, chemotherapeutic agents are co-administered with hormonal and radiation therapy, along with the disclosed variant PA molecules, for treatment of a localized prostate carcinoma.

Conservative substitution: One or more amino acid substitutions (for example 2, 5 or 10 residues) for amino acid residues having similar biochemical properties. Typically, conservative substitutions have little to no impact on the activity of a resulting polypeptide. For example, ideally, a modified PA peptide including one or more conservative substitutions retains proaerolysin activity. A polypeptide can be produced to contain one or more conservative substitutions by manipulating the nucleotide sequence that encodes that polypeptide using, for example, standard procedures such as site-directed mutagenesis or PCR.

Substitutional variants are those in which at least one residue in the amino acid sequence has been removed and a different residue inserted in its place. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

Permissive substitutions are non-conservative amino acid substitutions, but also do not significantly alter proaerolysin activity. An example is substitution of Cys for Ala at position 300 of SEQ ID NO: 2 or 4.

Further information about conservative substitutions can be found in, among other locations in, Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988), WO 00/67796 (Curd et al.) and in standard textbooks of genetics and molecular biology.

In one example, such variants can be readily selected for additional testing by performing an assay (such as those described in Examples 2-5) to determine if the variant retains variant PA activity.

Comprises: A term that means "including." For example, "comprising A or B" means including A or B, or both A and B, unless clearly indicated otherwise.

Deletion: The removal of a sequence of a nucleic acid, for example DNA, the regions on either side being joined together.

DNA: Deoxyribonucleic acid. DNA is a long chain polymer which comprises the genetic material of most living organisms (some viruses have genes comprising ribonucleic acid, RNA). The repeating units in DNA polymers are four different nucleotides, each of which comprises one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Enhance: To improve the quality, amount, or strength of something. In one embodiment, a therapy enhances the ability of a subject to reduce tumors, such as a prostate carcinoma, in the subject if the subject is more effective at fighting tumors. In another embodiment, a therapy enhances the ability of an agent to reduce tumors, such as a prostate carcinoma, in a subject if the agent is more effective at reducing tumors. Such enhancement can be measured using the methods disclosed herein, for example determining the decrease in tumor volume (see Example 5).

Functional Deletion: A mutation, partial or complete deletion, insertion, or other variation made to a gene sequence which renders that part of the gene sequence non-functional.

For example, functional deletion of a PA binding domain results in a decrease in the ability of PA to bind to and concentrate in the cell membrane. This functional deletion can be reversed by inserting another functional binding domain into proaerolysin, such as a prostate-specific binding domain, for example, an LHRH peptide.

Examples of methods that can be used to functionally delete a proaerolysin binding domain, include, but are not limited to: deletion of about amino acids 1-83 of SEQ ID NO: 2 or fragments thereof, such as about amino acids 45-66 of SEQ ID NO: 2, or inserting one or more of the following mutations into a variant proaerolysin sequence W45A, I47E, M57A, Y61A, K66Q (amino acid numbers refer to SEQ ID NO: 2) (for example, see Mackenzie et al. *J. Biol. Chem.* 274: 22604-22609, 1999).

In another example, functional deletion of a native PA furin cleavage site results in a decrease in the ability of PA to be cleaved and activated by furin, when compared to a wild-type PA molecule.

Immobilized: Bound to a surface, such as a solid surface. A solid surface can be polymeric, such as polystyrene or polypropylene. In one embodiment, the solid surface is in the form of a bead. In another embodiment, the surface includes a modified PA toxin, and in some examples further includes one or more prostate-specific binding ligands, such as LHRH peptide, PSMA antibody, and PSMA single chain antibody. Ideally, the modified PA toxin is liberated from the bead once the bead reaches the prostate cell target. Methods of immobilizing peptides on a solid surface can be found in WO 94/29436, and U.S. Pat. No. 5,858,358.

Examples of how the molecules can be attached to the bead include, but are not limited to: PA toxin-PSA cleavage site-bead-prostate binding ligand; or prostate binding ligand-bead-PSA site-PA toxin-PSA cleavage site-inhibitor.

Isolated: An "isolated" biological component (such as a nucleic acid molecule or protein) has been substantially separated or purified away from other biological components in the cell of the organism in which the component naturally occurs (i.e. other chromosomal and extrachromosomal DNA and RNA). Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins.

An isolated cell is one which has been substantially separated or purified away from other biological components of the organism in which the cell naturally occurs.

Malignant: Cells which have the properties of anaplasia invasion and metastasis.

Mammal: This term includes both human and non-human mammals. Similarly, the term "subject" includes both human and veterinary subjects. Examples of mammals include, but are not limited to: humans, pigs, cows, goats, cats, dogs, rabbits and mice.

Neoplasm: Abnormal growth of cells.

Normal Cell: Non-tumor cell, non-malignant, uninfected cell.

Oligonucleotide: A linear polynucleotide sequence of up to about 200 nucleotide bases in length, for example a polynucleotide (such as DNA or RNA) which is at least about 6 nucleotides, for example at least 15, 50, 100 or 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame): A series of nucleotide triplets (codons) coding for amino acids without any termination codons. These sequences are usually translatable into a peptide.

Polynucleotide: A linear nucleic acid sequence of any length. Therefore, a polynucleotide includes molecules which are at least 15, 50, 100, 200, 400, 500, 1000, 1100, or 1200 (oligonucleotides) and also nucleotides as long as a full-length cDNA or chromosome.

Proaerolysin: The inactive protoxin of aerolysin. The cDNA and protein of a wild-type or native proaerolysin are shown in SEQ ID NOS: 1 and 2, respectively.

In one example, a variant or modified proaerolysin molecule includes a prostate-specific protease cleavage site, such as a PSA-specific cleavage site, which permits activation of the variant PA in the presence of a prostate-specific protease such as PSA, PMSA, or HK2 (for example, see FIGS. 5C-I). In one example, a prostate-specific protease cleavage site is inserted into the native furin cleavage site of PA, such that PA is activated in the presence of a prostate-specific protease, but not furin (for example see FIGS. 5D-I). Alternatively, the furin cleavage site can be functionally deleted using mutagenesis of the six amino acid sequence, and insertion of a prostate-specific protease cleavage sequence (for example, see FIG. 5C). In another example, a variant PA molecule further includes deletion or substitution of one or more, such as at least two, of the native PA amino acids. In yet another example a variant PA molecule further includes another molecule (such as an antibody or peptide) linked or added to (or within) the variant PA molecule. In another example, a variant PA molecule includes a prostate-tissue specific binding domain.

In another example, a variant PA molecule further includes a functionally deleted binding domain (about amino acids 1-83 of SEQ ID NO: 2). Functional deletions can be made using any method known in the art, such as deletions, insertions, mutations, or substitutions. Examples include, but are not limited to deleting the entire binding domain (or portions thereof, (for example, see FIGS. 5G-I), or introduction of point mutations (such as those described above, (for example, see FIGS. 5D-F), which result in a binding domain with decreased function. For example, a PA molecule which has a functionally deleted binding domain (and no binding sequence substituted therefor), will have a decreased ability to accumulate in a cell membrane, and therefore lyse cells at a slower rate than a wild-type PA sequence (for example, see FIG. 5D). Also disclosed are variant PA molecules in which the native binding domain is functionally deleted and replaced with a prostate-tissue specific binding domain as described below (for example, see FIGS. 5E-I).

In another example, a variant or modified PA molecule includes a furin cleavage site, and a functionally deleted binding domain which is replaced with a prostate-tissue specific binding domain (for example, see FIGS. 5J-M). Such variant PA molecules are targeted to prostate cells via the prostate-tissue specific binding domain, and activated in the presence of furin.

Particular non-limiting examples of variant PSA proteins are shown in SEQ ID NOS: 4, 7, 10, 13, 24, and 25.

Modified PA activity is the activity of an agent in which the lysis of cells is affected. Cells include, but are not limited to prostate-specific protease secreting cells, such as PSA-secreting cells, such as prostate cancer cells, such as slow-proliferating prostate cancer cells. Agents include, but are not limited to, modified PA proteins, nucleic acids, specific binding agents, including variants, mutants, polymorphisms, fusions, and fragments thereof, disclosed herein. In one example, modified PA activity is said to be enhanced when modified PA proteins or nucleic acids, when contacted with a PSA-secreting cell (such as a prostate cancer cell), promote lysis and death of the cell, for example by at least 10%, or for example by at least 25%, 50%, 100%, 200% or even 500%, when compared to lysis of a non-PSA producing cell. In other examples, modified PA activity is said to be enhanced when modified PA proteins and nucleic acids, when contacted with a tumor, decrease tumor cell volume, such as a prostate tumor, for example by at least 10% for example by at least 20%, 30%, 40%, 50%, 60%, 70%, 75%, 80%, 85%, 90%, 95%, 98%, or even 100% (complete elimination of the tumor).

Assays which can be used to determine if an agent has modified PA activity are described herein, for example in Examples 2-5 and 9. For example, a modified PA peptide can be assessed for its ability to specifically lyse PSA-producing cells (Examples 2 and 5), be stable in human plasma (Example 3), be an efficient substrate for the enzymatic activity of PSA (Example 9). Functional protein activity could be detected by the preferential lysis of PSA-producing cells versus non-PSA-producing cells, decreasing prostate tumor volume, having a decreased toxicity when compared to wild-type PA, and having an increased stability in blood when compared to wild-type PA.

Similar assays can be used to determine if any modified PA agent disclosed herein can decrease tumor volume (such as a prostate tumor) and specifically lyse PSA-producing cells. For example, the modified PA peptides shown in SEQ ID NOS: 4, 24, and 25, are expected to decrease prostate tumor volume. Any of these assays can be modified by using in vivo expression of a modified PA gene, and variants, fusions, and fragments thereof, instead of administration of purified proteins.

Promoter: An array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Prostate-specific promoter: A promoter responsive to testosterone and other androgens, which therefore promotes gene expression in prostate cells. Examples include, but are not limited to the probasin promoter; the prostate specific antigen (PSA) promoter; the prostate specific membrane antigen (PSMA) promoter; and the human glandular kallikrein 2 (HK2) promoter.

Prostate-specific protease cleavage site: A sequence of amino acids which is recognized and specifically and efficiently hydrolyzed (cleaved) by a prostate-specific protease. Examples include, but are not limited to a PSA-specific cleavage site, a PSMA-specific cleavage site and an HK2-specific cleavage site.

A PSA-specific cleavage site is a sequence of amino acids which is recognized and specifically and efficiently hydrolyzed (cleaved) by prostate specific antigen (PSA). Such peptide sequences can be introduced into other molecules, such as PA, to produce prodrugs that are activated by PSA. Upon activation of the modified PA by PSA, PA is activated and can exert its cytotoxicity. Examples of PSA-specific cleavage sites, include, but are not limited to are those shown in SEQ ID NOS: 5, 8, 11, and 14-21, those disclosed in U.S. Pat. Nos. 5,866,679 to DeFeo-Jones et al., 5,948,750 to Garsky et al., 5,998,362 to Feng et al., 6,265,540 to Isaacs et al., 6,368,598 to D'Amico et al., and 6,391,305 to Feng et al., (all herein incorporated by reference).

Particular examples of PSMA-specific cleavage sites can be found in WO/0243773 to Isaacs and Denmeade (herein incorporated by reference). Particular examples of HK2-specific cleavage sites are disclosed in WO/0109165 to Denmeade et al. (herein incorporated by reference).

Prostate tissue-specific binding domain: A molecule, such as a peptide ligand, toxin, or antibody, which has a higher specificity for prostate cells than for other cell types. In one example, a prostate tissue specific binding domain has a lower $K_D$ in prostate tissue or cells than in other cell types, (i.e. binds selectively to prostate tissues as compared to other normal tissues of the subject), for example at least a 10-fold lower $K_D$, such as an at least 20-, 50-, 75-, 100- or even 200-fold lower $K_D$. Such sequences can be used to target an agent, such as a variant PA molecule, to the prostate. Examples include, but are not limited to: antibodies which recognize proteins that are relatively prostate-specific such as PSA, PSMA, hK2, prostasin, and hepsin; ligands which have prostate-selective receptors such as natural and synthetic luteinizing hormone releasing hormone (LHRH); and endothelin (binding to cognate endothelin receptor).

Purified: The term "purified" does not require absolute purity; rather, it is intended as a relative term. Thus, for example, a substantially purified protein or nucleic acid preparation (such as the modified PA toxins disclosed herein) is one in which the protein or nucleic acid referred to is more pure than the protein in its natural environment within a cell or within a production reaction chamber (as appropriate). For example, a preparation of a modified PA protein is purified if the protein represents at least 50%, for example at least 70%, of the total protein content of the preparation. Methods for purification of proteins and nucleic acids are well known in the art. Examples of methods that can be used to purify a protein, such as a modified PA, include, but are not limited to the methods disclosed in Sambrook et al. (*Molecular Cloning: A Laboratory Manual*, Cold Spring Harbor, N.Y., 1989, Ch. 17).

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. A recombinant protein is one that results from expressing a recombinant nucleic acid encoding the protein.

Sample: Biological samples containing genomic DNA, cDNA, RNA, or protein obtained from the cells of a subject, such as those present in peripheral blood, urine, saliva, semen, tissue biopsy, surgical specimen, fine needle aspirates, amniocentesis samples and autopsy material. In one example, a sample includes prostate cancer cells obtained from a subject.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, 75%, 80%, 85%, 90%, 95%, or even 99% sequence identity. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

Protein homologs are typically characterized by possession of at least 70%, such as at least 75%, 80%, 85%, 90%, 95% or even 98% sequence identity, counted over the full-length alignment with the amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG.

One of skill in the art will appreciate that these sequence identity ranges are provided for guidance only; it is possible that strongly significant homologs could be obtained that fall outside the ranges provided. Provided herein are the peptide homologs described above, as well as nucleic acid molecules that encode such homologs.

Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous peptides can, for example, possess at least 75%, 80%, 90%, 95%, 98%, or 99% sequence identity determined by this method. When less than the entire sequence is being compared for sequence identity, homologs can, for example, possess at least 75%, 85% 90%, 95%, 98% or 99% sequence identity over short windows of 10-20 amino acids. Methods for determining sequence identity over such short windows can be found at the NCBI web site. One of skill in the art will appreciate that these sequence identity ranges are provided for guidance only; it is possible that significant homologs or other variants can be obtained that fall outside the ranges provided.

Subject: Living multicellular vertebrate organisms, a category which includes, both human and veterinary subjects that require an increase in the desired biological effect. Examples include, but are not limited to: humans, apes, dogs, cats, mice, rats, rabbits, horses, pigs, and cows.

Therapeutically Effective Amount: An amount sufficient to achieve a desired biological effect, for example an amount that is effective to decrease the size (i.e. volume), side effects and/or metastasis of prostate cancer. In one example, it is an amount sufficient to decrease the symptoms or effects of a prostate carcinoma, such as the size of the tumor. In particular examples, it is an amount effective to decrease the size of a prostate tumor and/or prostate metastasis by at least 30%, 40%, 50%, 70%, 80%, 90%, 95%, 99% or even 100% (complete elimination of the tumor).

In particular examples, it is an amount of a modified PA molecule effective to decrease a prostate tumor and/or an amount of prostate cancer cells lysed by a modified PA, such as in a subject to whom it is administered, for example a subject having one or more prostate carcinomas. In other examples, it is an amount of a modified PA molecule and/or an amount of prostate cancer cells lysed by such a modified PA molecule, effective to decrease the metastasis of a prostate carcinoma.

In one embodiment, the therapeutically effective amount also includes a quantity of modified PA and/or an amount of prostate cancer cells lysed by a modified PA sufficient to achieve a desired effect in a subject being treated. For instance, these can be an amount necessary to improve signs and/or symptoms a disease such as cancer, for example prostate cancer.

An effective amount of modified PA and/or prostate cancer cells lysed by such a modified PA molecule can be administered in a single dose, or in several doses, for example daily, during a course of treatment. However, the effective amount of will be dependent on the subject being treated, the severity and type of the condition being treated, and the manner of administration. For example, a therapeutically effective amount of modified PA can vary from about 1-10 mg per 70 kg body weight, for example about 2.8 mg, if administered iv and about 10-100 mg per 70 kg body weight, for example about 28 mg, if administered intraprostatically or intratumorally. In addition, a therapeutically effective amount of prostate cancer cells lysed by PA (variant or wild-type) can vary from about $10^6$ to $10^8$ cells.

Therapeutically effective dose: In one example, a dose of modified PA sufficient to decrease tumor cell volume, such as a prostate carcinoma, in a subject to whom it is administered, resulting in a regression of a pathological condition, or which is capable of relieving signs or symptoms caused by the condition. In a particular example, it is a dose of modified PA sufficient to decrease metastasis of a prostate cancer.

In yet another example, it is a dose of cell lysate resulting from contact of cells with a modified PA sufficient to decrease tumor cell volume, such as a prostate carcinoma, in a subject to whom it is administered, resulting in a regression of a pathological condition, or which is capable of relieving signs or symptoms caused by the condition. In a particular example, it is a dose of cell lysate resulting from contact of cells with a modified or wild-type PA sufficient to decrease metastasis of a prostate cancer.

Tumor: A neoplasm. Includes solid and hematological (or liquid) tumors.

Examples of hematological tumors include, but are not limited to: leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (including low-, intermediate-, and high-grade), multiple myeloma, Waldenstrdm's macroglobulinemia, heavy chain disease, myelodysplastic syndrome, mantle cell lymphoma and myelodysplasia.

Examples of solid tumors, such as sarcomas and carcinomas, include, but are not limited to: fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transgenic Cell: Transformed cells which contain foreign, non-native DNA.

Transgenic mammal: Transformed mammals which contain foreign, non-native DNA. In one embodiment, the non-native DNA is a modified PA which includes a PSA cleavage site, such as SEQ ID NO: 3, or a nucleic acid sequence which encodes for a protein shown in SEQ ID NOS: 24 or 25.

Variants or fragments or fusion proteins: The production of modified PA protein can be accomplished in a variety of ways (for example see Examples 12 and 16). DNA sequences which encode for a modified PA protein or fusion protein, or a fragment or variant of a protein (for example a fragment or variant having 80%, 90% or 95% sequence identity to a modified PA) can be engineered to allow the protein to be expressed in eukaryotic cells or organisms, bacteria, insects, and/or plants. To obtain expression, the DNA sequence can be altered and operably linked to other regulatory sequences. The final product, which contains the regulatory sequences and the therapeutic modified PA protein, is referred to as a vector. This vector can be introduced into eukaryotic, bacteria, insect, and/or plant cells. Once inside the cell the vector allows the protein to be produced.

A fusion protein which includes a modified PA, (or variants, polymorphisms, mutants, or fragments thereof) linked to other amino acid sequences that do not inhibit the desired activity of the protein, for example the ability to lyse PSA-secreting cells. In one example, the other amino acid sequences are no more than 5, 6, 7, 8, 9, 10, 20, 30, or 50 amino acid residues in length.

One of ordinary skill in the art will appreciate that the DNA can be altered in numerous ways without affecting the biological activity of the encoded protein. For example, PCR can be used to produce variations in the DNA sequence which encodes a variant PA toxin. Such variants can be variants optimized for codon preference in a host cell used to express the protein, or other sequence changes that facilitate expression.

Vector: A nucleic acid molecule as introduced into a host cell, thereby producing a transformed host cell. A vector can include nucleic acid sequences that permit it to replicate in the host cell, such as an origin of replication. A vector can also include one or more selectable marker genes and other genetic elements known in the art.

Additional definitions of terms commonly used in molecular genetics can be found in Benjamin Lewin, Genes V published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Variant Proaerolysin Molecules

Bacterial toxins, such as aerolysin produced by *Aeromonas hydrophilia* and α-hemolysin produced by *Staph aureus*, are beta-sheet proteins that oligomerize in the plasma membrane to produce pores that lead to rapid cytolytic cell death (FIG. 1). Pore formation physically disrupts the cell membranes, and results in death of cells in all phases of the cell cycle, including non-proliferating cells (i.e. GO arrested). However, wild-type aerolysin kills cells indiscriminately. Herein disclosed is an inactive protoxin form of aerolysin (a variant PA) that can be targeted to, and activated by, prostate cancer specific proteins. One advantage of the disclosed variant PA molecules for treatment of localized and metastatic prostate cancer, is that it combines a proliferation independent therapy with prostate-specific drug delivery, resulting in minimal side effects to patients. One skilled in the art will understand that other protoxins, such as *Clostridium septicum* alpha toxin, *Bacillus thuringiensis* delta-toxin, and human perforin, can be substituted for proaerolysin.

Disclosed herein are variant PA molecules, including both DNA and protein sequences, which include a prostate-specific protease cleavage sequence. Examples of prostate-specific protease cleavage sequences include, but are not limited to: PSA, PSMA, and HK2 cleavage sequences. The prostate-specific protease cleavage sequence functionally replaces the native furin cleavage site of PA (for example, see FIGS. 5B-I). This replacement results in a proaerolysin variant that only becomes cytolytically active in the presence of enzymatically active protease, such as PSA, PSMA, or hK2. PSA is a serine protease with the ability to recognize and hydrolyze specific peptide sequences. It is secreted by normal and malignant prostate cells in an enzymatically active form and becomes inactivated upon entering the circulation. Since neither blood nor normal tissue other than the prostate contains enzymatically active PSA, the proteolytic activity of PSA was used to activate protoxins at sites of prostate cancer. Any PSA, PSMA, or hK2 cleavage site can be used. Examples of PSA cleavage sites include, but are not limited to, those shown in SEQ ID NOS: 5, 8, 11, and 14-21. In a particular example, the PSA cleavage site includes SEQ ID NO: 5.

In some examples, the furin cleavage site of PA (amino acids 427-432 of SEQ ID NO: 2) is deleted and a prostate-specific protease cleavage site, such as a PSA cleavage site, is inserted (for example, see FIG. 5B). In other examples, the furin cleavage site of PA is mutated and a prostate-specific protease cleavage site, such as a PSA cleavage site, inserted with in, or added to the N- or C-terminus of the furin site (for example, see FIG. 5C).

Also disclosed are variant PA molecules in which the PA binding domain is functionally deleted (for example, see FIGS. 5D-M). Such variant PA molecules can contain a native furin cleavage site (for example, see FIGS. 5J-M), whereby targeting to prostate cells is achieved by functionally replacing the PA binding domain with a prostate-tissue specific binding domain. Alternatively, variant PA molecules contain a prostate-specific protease cleavage site (for example, see FIGS. 5D-I), whereby activation of the protoxin primarily occurs in cells that secrete a prostate-specific protease. The PA binding domain includes about amino acids 1-83 of SEQ ID NO: 2. The binding domain can be functionally deleted using any method known in the art, for example by deletion of all or some of the amino acids of the binding domain, such as deletion of amino acids 1-83 of SEQ ID NO: 2 or 4 (for example see FIG. 5G), or such as deletion of one or more amino acids shown as amino acids 45-66 of SEQ ID NO: 2 or 4 (for example see FIG. 5D where the * represents one or more deletions). In other examples, the binding domain is functionally deleted by introduction of one or more site-specific mutations into the variant PA sequence, such as W45A, 147E, M57A, Y61A, and K66Q of SEQ ID NO: 2 or 4 (for example see FIG. 5D, where the * represents one or more mutations).

Variant PA molecules which include a prostate-tissue specific binding domain which functionally substitutes for the native PA binding domain are disclosed (for example, see FIGS. 5E, 5F, 5H and 5I-M). The use of one or more prostate-tissue specific binding domains can increase targeting of the disclosed variant PA molecules to the prostate cells and its metastases. Several prostate-tissue specific binding domains are known. Examples include, but are not limited to a luteinizing hormone releasing hormone (LHRH) sequence, such as those shown in SEQ ID NOS: 22 and 23, and antibodies that recognize PSA and/or PSMA.

One or more prostate-tissue specific binding domains can be linked to one or more amino acids of the disclosed variant PA molecules, but ideally, do not interfere significantly with the ability of the variant PA to be activated by a prostate-specific protease such as PSA, and the ability to form pores in cell membranes. For example, prostate tissue specific binding domains can be linked or inserted at an N- and/or C-terminus of a variant PA (for example, see FIGS. 5E and 5H). In some examples, the native binding domain of PA is deleted (i.e. amino acids 1-83 of SEQ ID NO: 2 or 4), such that attachment or linking of a prostate tissue specific binding domain to the N-terminus results in attachment to amino acid 84 of SEQ ID NO: 2 or 4 (for example, see FIGS. 5H and 5L). In other examples, smaller deletions or point mutations are introduced into the native binding domain of PA, such that attachment or linking of a prostate tissue specific binding domain to the N-terminus results in attachment to amino acid 1 of SEQ ID NO: 2 or 4 (or whichever amino acid is N terminal following functional deletion of the native PA binding domain) (for example, see FIGS. 5E and 5I). In some examples, the N-terminal amino acid of PA is changed to a Cys or other amino acid to before attaching a prostate-tissue specific binding domain, to assist in linking the prostate-tissue specific binding domain to the variant PA protein.

Alternatively or in addition, one or more prostate tissue specific binding domains can be attached or linked to other amino acids of a variant PA molecule, such as amino acid 215 or 300 of SEQ ID NO: 2 or 4 (for example, see FIGS. 5F, 5I, 5K and 5M). In some examples, a Cys amino acid replaces the native amino acid at that position. For example, the following changes can be made to SEQ ID NO: 2 or 4: Tyr215Cys or Ala300Cys. In one example, where the prostate tissue specific binding domain is an antibody, crosslinking can be used to attach antibodies to a variant PA, for example by reacting amino groups on the antibody with cysteine located in the PA variant (such as amino acids Cys19, Cys75, Cys159, and/or Cys164 of SEQ ID NO: 2).

Also disclosed are particular variant PA molecules, such as those shown in SEQ ID NOS: 3, 4, 6, 7, 9, 10, 12, 13, 24 and 25.

In some examples the disclosed variant PA molecules are linked or immobilized to a surface, such as a bead. The bead can also include a prostate-specific ligand to enhance targeting to a prostate cell, such as a localized or metastasized prostate cancer cell.

Treatment of Prostate Cancer Using Modified Proaerolysin

The variant PA molecules disclosed and discussed above are specifically activated to potent cytotoxins within prostate cancer sites via the proteolytic activity of prostate-specific proteases such as PSA, PSMA, and hK2. Targeting in some examples is achieved by including one or more prostate-tissue specific binding domains, such as LHRH peptide which can bind to its cognate LHRH receptor expressed by prostate cancer cells, or PSMA or LHRH antibodies, which can bind to PSMA or LHRH expressed on the surface of prostate cancer cells. One skilled in the art will recognize that the use of a variant PA molecule which includes a furin cleavage site and an LHRH peptide or antibody, can be used to treat other cancers which express LHRH receptors, such as melanoma and cancers of the breast, ovary and lung, using the variant PA molecules and methods disclosed herein. Furthermore, one skilled in the art will recognize that the use of a variant PA molecule which includes a furin or PSMA cleavage site, and/or a PSMA antibody, can be used to treat other cancers in which PSMA is expressed (e.g. in the vasculature of the tumor), such as cancers of the breast, colon, kidney, bladder and brain, using the variant PA molecules and methods disclosed herein.

The disclosed variant PA molecules, such as nucleic acids and/or proteins, can be administered locally or systemically using any method known in the art, to subjects having localized or metastatic prostate cancer. In addition, the disclosed variant PA molecules can be administered to a subject for immunostimulatory therapy. Due to the specificity of binding and activation of the disclosed variant PA molecules, local and systemic administration should have minimal effect on a patient's normal tissues and ideally produce little to no side effects.

In one example, the disclosed variant PA molecules are injected into the prostate gland (intraprostatically) and/or into the prostate tumor (intratumorally) in a subject having prostate cancer, such as a localized tumor. Such localized injection and subsequent lysis of prostate cancer cells within the prostate gland can produce an immunostimulatory effect leading to a decrease or elimination of micrometastatic disease in treated subjects. In this way, systemic disease is treated or reduced through a minimally toxic, locally applied therapy.

In addition, or alternatively, the disclosed variant PA molecules can be administered systemically, for example intravenously, intramuscularly, subcutaneously, or orally, to a subject having prostate cancer, such as a metastatic prostate tumor. Systemic therapy can also have an immunostimulatory anti-tumor effect. The disclosed variant PA molecules which include a PSA-cleavage site are not hydrolyzed by serum proteases or enzymatically inactive PSA within the blood. Instead, the unhydrolyzed disclosed variant PA molecules are delivered via the blood to the extracellular fluid within metastatic cancer deposits where they can be hydrolyzed to the active therapeutic toxin by the enzymatically active PSA secreted by these prostate cancer cells. Once hydrolyzed, the liberated toxin enters PSA-producing and non-producing bystander cells in the immediate vicinity due to its high membrane penetrating ability and induces the cytolytic death of these cells.

An additional method for systemically treating prostate cancer in a subject is also disclosed. In this method, prostate cancer cells are removed from the subject having prostate cancer, such as a metastatic prostate tumor. Alternatively or in addition, established prostate cancer cell lines can be used. Examples of prostate cancer cell lines that can be used include, but are not limited to: PSA-producing cells such as LNCaP (such as ATTC Nos. CRL-1740 and CRL-10995) and CWR22R (ATCC No. CRL-2505 and Nagabhushan et al., Cancer Res. 56(13):3042-6, 1996), or PSA non-producing cells such as PC-3 (ATCC No. CRL-1435) and DU 145 (ATCC No. HTB-81). The removed cells or cell lines are incubated or contacted with the disclosed variant PA molecules. This incubation results in lysis of the cells by the variant PA molecules, and production of a cell lysate which is administered to the subject. In one example, the method further includes administration of immunostimulatory factors, lysates from prostate cancer cells engineered to produce immunostimulatory factors, and/or irradiated prostate cancer cells (including prostate cancer cells engineered to produce immunostimulatory factors). Examples of immunostimulatory factors include, but are not limited to: granulocyte macrophage colony stimulatory factor (GM-CSF); members of the interleukin family of proteins such as but not limited to interleukin-2 and interleukin-6, granulocyte colony stimulatory factor (G-CSF); and members of interferon family such as interferon alpha, beta or gamma. Administration of such materials to a subject can be simultaneous with the cell lysate (co-administration), before administration of the cell lysate, and/or subsequent to administration of the cell lysate.

In one example, such administration enhances the ability of a subject to decrease the volume of a prostate tumor and/or a metastatic tumor. For example, the disclosed methods can reduce prostate tumor cell volume and/or a metastatic tumor cell volume, such as by at least 10%, for example by at least 20% or more. In addition, the disclosed methods can result in a decrease in the symptoms associated with a prostate tumor and/or a metastatic prostate tumor.

The disclosed variant PA molecules can be administered as a single modality therapy or used in combination with other therapies, such as radiation therapy and/or androgen ablative therapies (such as LHRH receptor agonists/antagonists, anti-androgens, estrogens, adrenal steroid synthesis inhibitors ketoconazole and aminoglutethimide). In addition, administration of the disclosed variant PA molecules can be alone, or in combination with a pharmaceutically acceptable carrier, and/or in combination with other therapeutic compounds, such as those that reduce the production of antibodies to the administered variant PA proteins (for example Rituximab and steroids) and other anti-tumor agents.

Disclosure of certain specific examples is not meant to exclude other embodiments. In addition, any treatments described herein are not necessarily exclusive of other treatment, but can be combined with other bioactive agents or treatment modalities.

EXAMPLE 1

Generation of PSA-Activated Proaerolysin Toxins

This example describes methods used to produce the variant proaerolysin toxins shown in Table 1, which are activated by PSA. One skilled in the art will understand that similar methods can be used to produce other variant proaerolysin proteins which are activated by PSA or any other prostate-specific protease. Such proteins can be produced by substituting the furin sequence of proaerolysin with a prostate-specific protease cleavage site, such as a PSA-specific cleavage sequence (see Example 9).

TABLE 1

PSA-specific proaerolysin variants

| Mutant (SEQ ID NO) | Change(s) made (SEQ ID NO) | Comparison to wt Proaerolysin ADSKVRRARSVDGAGQGLRLEIPLD (aa 424-448 of SEQ ID NO:2) |
|---|---|---|
| PSA-PA1 (3 & 4) | KVRRAR (aa 427-432 of SEQ ID NO:2) changed to HSSKLQ (5) | ADSHSSKLQSVDGAGQGLRLEIPLD (aa 424-448 of SEQ ID NO:4) |

TABLE 1-continued

PSA-specific proaerolysin variants

| Mutant (SEQ

PSA-PA1 toxin was tested against PSA-producing LNCaP cells (American Type Culture Collection, Manassas, Va.) and non-PSA-producing TSU cells (Dr. T. Itzumi, Teikyo University, Japan). Cells were incubated in the presence of $10^{-12}$ M to $10^{-6}$ M toxin for 24 hours. Subsequently, cells were counted and scored for percent viable cells based on ability to exclude Trypan Blue. Concentration required to kill 50% of cells ($IC_{50}$) was determined for the toxin against both LNCaP and TSU lines.

The $LD_{50}$ for PSA-PA1 against PSA-producing cells was $10^{-10}$ M. In contrast, against non-PSA producing TSU cells the $LD_{50}$ was $\sim 5 \times 10^{-8}$ M. This result demonstrates that the PSA-PA1 toxin is specifically activated by PSA as evidenced by a 500-fold difference in toxicity against PSA-producing versus non-PSA producing human cancer cell lines.

EXAMPLE 3

PSA-PA1 is Not Activated in Blood Containing PSA

The disclosed prostate-specific protease-activated variant proaerolysin peptides, such as those described in Example 1, can be injected intraprostatically (or intratumorally) as local therapy for prostate cancer. The toxin can also be injected intravenously (or intramuscularly) as systemic therapy for metastatic prostate cancer. Those variant PA molecules which include a PSA site should not be activated in blood, because PSA is enzymatically inactivated in the blood due to the presence of a large molar excess of serum protease inhibitors such as $\alpha_1$-antichymotrypsin and $\alpha_2$-macroglobulin.

To test for non-specific activation of PSA-PA1 by other serum proteases and PSA in human serum, a sensitive hemolysis assay was performed as follows. Red blood cells (RBCs, 2% v/v) were added to plasma or buffer containing PSA-PAL toxin±PSA. The extent of hemolysis was assayed by measuring release of hemoglobin into the supernatant. Addition of 0.1% Triton results in 100% hemolysis within a few seconds and was used as the positive control. Amount of hydrolysis was expressed as a ratio of sample absorbance at 540 nm to absorbance of Triton treated sample. Pre-incubation of the PSA-PA1 toxin ($10^{-8}$ M) with PSA in aqueous buffer alone for 1 hour prior to adding RBCs resulted in ~45% hemolysis (FIG. 2).

To determine whether PSA-PA1 becomes activated in human plasma, PSA-PA1 toxin ($10^{-8}$ M) was incubated in 50% human plasma for 1 hour. In a related experiment, excess PSA (10,000 ng/ml) was first added to the human plasma and allowed to incubate for several hours. The PSA-PA1 containing plasma±PSA was then incubated with human RBCs (2% v/v). The addition of PSA-PA1 to human plasma, or human plasma spiked with high concentration of PSA, resulted in no appreciable hemolysis (i.e. <1% of Triton control) (FIG. 2). These results demonstrate that PSA-PA1 can be administered systemically without any significant activation in the blood, even if the blood contains measurable PSA.

EXAMPLE 4

In Vitro and In Vivo Toxicity Proaerolysin Variants

This example describes methods used to determine the in vitro and in vivo toxicity of the disclosed modified proaerolysin proteins. Such methods can be used to measure the toxicity of any prostate-specific protease-cleavable proaerolysin variant protein.

To determine in vitro toxicity, a cell viability assay was performed as follows. El4 mouse T-cell lymphoma cells (ATCC TIB-39) were cultured at $10^{+5}$ cells per well in MTS/PMS Cell Titer 96 (Promega). Proaerolysin variants at $1 \times 10^{-13}$ M-$1 \times 10^{-7}$ M was added as shown in FIG. 3, and incubated with the cells for 4 hours at 37° C. Cell viability was subsequently determined by reading the plate on a plate reader, as directed by the manufacturer of the MTS/PMS kit. As shown in FIG. 3, the proaerolysin variants are less toxic than wild-type proaerolysin, with an $LC_{50}$ of $4 \times 10^{-9}$ (PSA-PA1), $1 \times 10^{-9}$ (PSA-1K), and $1 \times 10^{-7}$ (PSA-PA2), in contrast to an $LC_{50}$ of $1.5 \times 10^{-10}$ for wild-type.

To determine in vivo toxicity, proaerolysin variants were administered to mice intravenously. Wild-type proaerolysin (SEQ ID NO: 2) was highly toxic to mice; a dose of 1 μg caused death within one hour and the $LD_{100}$ at 24 hours (i.e. the dose that kills 100% of animals within 24 hours) following a single IV injection was 0.1 μg. In contrast, the $LD_{100}$ of PSA-PA1 (SEQ ID NO: 4) at 24 hours post injection was 25-fold higher (i.e. 2.5 μg total dose).

EXAMPLE 5

PSA-PA1 Reduces PSA-Secreting Tumor Cell Volume

On the basis of the toxicity data described in Example 4, a series of LNCaP bearing mice (human LNCaP prostate cancer xenografts which produce PSA) and a series of SN12C bearing mice (control mice which have a human renal carcinoma xenograft which does not produce PSA) were administered a single 100 μl intratumoral injection of 0.25-25 μg PSA-PA1 (0.1-10 times the $LD_{100}$ dose). At 48 hours post injection, tumors were harvested, fixed and stained with H&E, and for Ki-67 (proliferative index) and Tunel (apoptotic index). The percent of tumor within sample was determined by calculating the ratio of viable tumor to total tumor area following image analysis of thin tumor sections.

Figure 4:
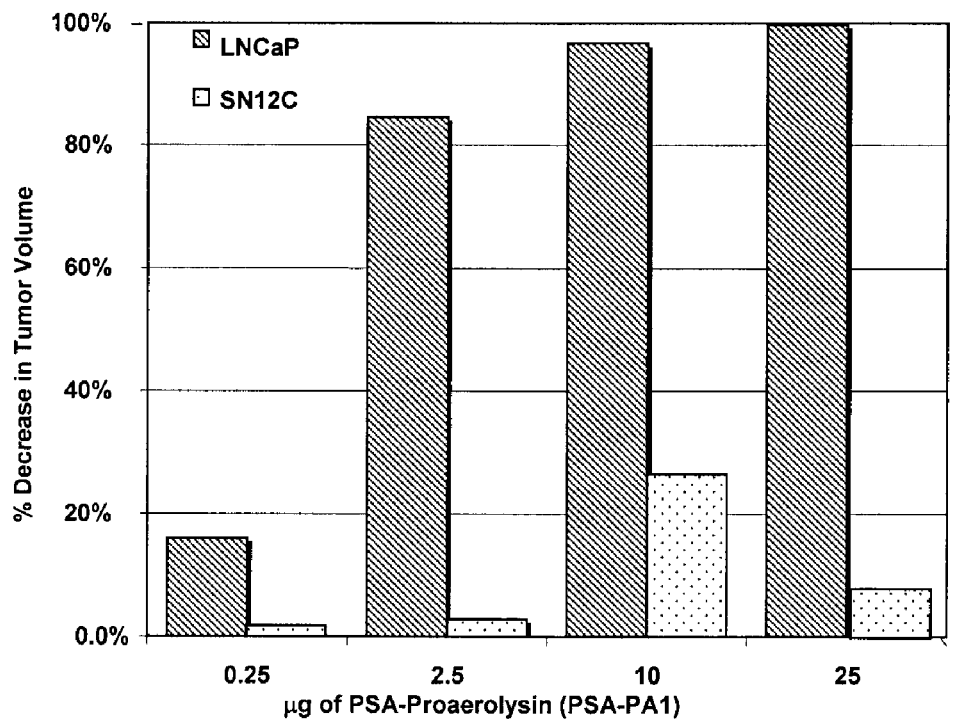
FIG. 4 is a bar graph comparing the specificity of PSA-PA1 in PSA-producing (LNCaP), and non-PSA producing (SN12C) tumors, in vivo.

As shown in FIG. 4, administration of 2.5-25 μg of PSA-PA1, reduced tumor cell volume by 85-99%, while <20% reduction was observed at 0.25 μg of PSA-PA1. In contrast, when mice bearing non-PSA producing SN12C human renal carcinoma xenografts (cells provided by Dr. Isaiah Fidler Anderson Cancer Center, Houston Tex.), were injected intratumorally with PSA-PA1, no significant reduction (i.e. <25%) in percent of viable tumor was observed over the same dose range (FIG. 4).

In control tumors (SN12C mice), the proliferative index was ~40% 48 hours post administration of intratumoral PSA-PA1. In contrast, in the responding PSA-PA1 treated tumors the percent of Ki-67 positive cells was <1% at 48 hours. In addition, in the control tumors the apoptotic index was <1% 48 hours post administration of intratumoral PSA-PA1, while in the PSA-PA1 treated tumors all cells were positive by 48 hours (i.e. apoptotic index>99%).

These results demonstrate that the PSA-PA1 toxin efficiently and rapidly kills PSA-producing cells and this cytotoxicity in vivo is specific and dependent on the presence of PSA present in the extracellular fluid of tumors.

EXAMPLE 6

Targeting the Protoxin Via Prostate-Specific Binding Domains

This example describes methods to generate and use variant prostate specific protease-activated proaerolysin toxins in which the wild-type (or native) PA binding domain (approximately amino acids 1-83 of SEQ ID NO: 2) is functionally replaced with a prostate-tissue specific binding domain, such as the LHRH peptide. The native binding domain of PA can be functionally deleted by any method known in the art, for example by deletion of about amino acids 1-83 of SEQ ID NO: 2 (or fragments thereof, such as 45-66), or by insertion of mutations which decrease the ability of PA to concentrate in cell membranes.

The N-terminal GPI-anchor protein binding domain of PA (approximately amino acids 1-83 of SEQ ID NO: 2) can be functionally deleted (for example by deletion of amino acids 1-83 or by insertion of mutations which render the domain non-functional) without significantly effecting pore-formation. A binding domain is needed, however, to concentrate the toxin in the cell membrane. Mutant proteins that lack the binding domain are cytolytic, but only when cells are exposed to several orders of magnitude higher concentrations of toxin. Most in vivo toxicity of wild type and variant PSA-activated PA described above in Example 4 is due to non-specific binding to GPI-anchor proteins expressed by most mammalian cells. To generate a more specific, and less systemically toxic protoxin, the non-specific GPI-anchor protein binding domain of proaerolysin can be functionally deleted and replaced with a prostate tissue-specific binding domain.

Antibodies

An example of a binding moiety that can be used to target a modified proaerolysin protein with high specificity to prostate tissue is a fusion protein which includes a single chain antibody to a prostate-specific membrane protein, and antibodies that recognize PSMA or LHRH fused to the toxin domains. Ideally, attachment of the antibody to a modified PA molecule will not significantly interfere with the ability of the molecule to bind to and concentrate in a cell membrane, resulting in cell death. Antibodies can be attached to the N- or C-terminus of a modified PA using gene fusion methods well known in the art (for example see Debinski and Pastan, *Clin. Cancer Res.* 1: 1015-22, 1995). For example, the antibody could replace the native small lobe of proaerolysin (amino acids 1-83 of SEQ ID NO: 2), or the antibody could be added to a PA molecule having mutations in the native binding domain. Such a modified proaerolysin can also include a PSA activation sequence to increase specificity. In one example, the antibody is a single chain antibody to PSMA fused to the toxin domain of PA.

Alternatively, antibodies or FAB fragments can be attached to a modified PA by covalent crosslinking (for example see Woo et al., *Arch. Pharm. Res.* 22(5):459-63, 1999 and Debinski and Pastan, *Clin. Cancer Res.* 1(9):1015-22, 1995). Crosslinking can be non-specific, for example by using a homobifunctional-lysine-reactive crosslinking agent, or it can be specific, for example by using a crosslinking agent that reacts with amino groups on the antibody and with cysteine located in the proaerolysin variant (such as amino acids Cys 19, Cys75, Cys159, and/or Cys164 of SEQ ID NO: 2).

Ligands

Other binding moieties that can be used are small peptide ligands that bind to their cognate receptor expressed on the membrane of prostate cancer cells. An example includes, but is not limited to, natural and synthetic luteinizing hormone releasing hormone (LHRH) agonist peptides (for example see Genbank Accession No. CAA25526 and SEQ ID NOS: 22 and 23), which bind with high affinity to LHRH receptors, and peptides that can bind selectively to PMSA. LHRH receptors are expressed by a high percentage of human prostate cancers, but not by hematopoeitic cells. This differential expression provides binding specificity.

It is known that certain residues of LHRH, such as the Gly at the 6th position (Gly6), can be substituted without compromising receptor binding affinity (Janaky et al., *Proc. Natl. Acad. Sci. USA* 89:972-6, 1992; Nechushtan et al., *J. Biol. Chem.*, 272:11597-603, 1997). Therefore, a variant PA toxin (in which the native binding domain is functionally deleted) can be produced which is covalently coupled to purified LHRH D-Lys6 (at the epsilon amine of this lysine).

LHRH D-Lys6 (SEQ ID NO: 23) can be attached to various portions of a modified proaerolysin protein having a functionally deleted binding domain. Ideally however, such placement will not significantly interfere with the ability of the toxin to insert into the membrane to form a pore. For example, the epsilon amine of the D-Lys6 analog can be coupled to the amino terminus of the modified proaerolysin via a dicarboxylic acid linker. Cleavage by furin or a prostate-specific protease (depending on which cleavage site is present in the proaerolysin peptide) will result in release of the C-terminal inhibitory portion while the toxin remains bound to the LHRH receptor.

Alternatively or in addition, the epsilon amine of the D-Lys6 analog of LHRH can be coupled directly to the C-terminal carboxyl of the modified proaerolysin lacking a functional wild type binding domain, by the addition of a Cys to the C-terminus of the modified PA, then crosslinking this Cys to the epsilon amine of the D-Lys6 analog of LHRH. This coupling will produce a derivative PA protein in which the LHRH peptide is attached to the C-terminal inhibitory domain of PA. Cleavage by furin or by a prostate specific protease, such as PSA, will liberate the toxin and leave the inhibitory fragment bound to the LHRH receptor. Therefore, pore formation should not be inhibited by tight binding to the receptor. In addition, recombinant fusion proteins can be produced in which modified LHRH peptides are fused to both the N- and C-terminus of the modified PA toxin lacking a functional native binding domain.

In other examples, a cysteine residue is introduced into the 6th position of the LHRH peptide and the peptide attached to the modified PA toxins via a disulfide bridge, for example at amino acids 215 and/or 300 of SEQ ID NO: 2, wherein amino acids 215 and/or 300 has been mutated to a cysteine. In another example, a recombinant protein is produced in which LHRH peptide is fused to the amino terminus of the modified PA toxin.

The resulting modified proaerolysin proteins which include a prostate tissue specific binding domain functionally substituted for the native PA binding domain, are tested in vitro and in vivo for binding specificity and toxin activation, using the methods described in Examples 1-5.

To demonstrate that prostate-tissue specific binding domains, such as LHRH or PSMA, can be functionally substituted for the native PA binding domain the following experiments can be performed. The methods described below describe the use of a molecule in which the native PA binding domain has been deleted, and LHRH linked to the resulting proaerolysin. However, similar methods can be used to test any variant PA molecule, such as molecules in which other prostate-tissue specific binding domains are used, and where the PA binding domain is mutated (for example by insertion of one or more of the following mutations: W45A, 147E, M57A, Y61A, K66Q, and W324A) instead of deleted.

LHRH-proaerolysin proteins containing the native PA furin activation sequence are produced. The specificity of binding of these toxins to LHRH receptor positive (LNCaP) and negative (TSU) cells is compared using methods described in Example 2. Both cell lines activate the wild type, furin-activation-site-containing PA. Therefore, while each line may activate the LHRH-proaerolysin proteins, the ideal peptide is one that is toxic at low concentrations to LHRH receptor positive cells. Using these methods, regions of proaerolysin to which the LHRH peptide can be attached without interfering with channel formation by the toxin are identified.

To demonstrate that LHRH-proaerolysin proteins both bind to LHRH receptor and are activated by PSA, toxins that contain a PSA-activation site instead of the furin site are generated using the methods described in Example 1. The activation of these toxins by LHRH positive, PSA-producing LNCaP cells is compared to activation by LHRH receptor negative, PSA non-producing TSU cells, using the methods described in Example 2.

LHRH-PSA-activated proaerolysin toxins are tested in vivo to demonstrate that introduction of the LHRH binding moiety results in decreased non-specific toxicity and increased targeting ability. As described above, the $LD_{100}$ of these toxins following a single intravenous injection is determined and compared to the corresponding non-LHRH containing, PSA-activated toxin, using the methods described in Example 4. Subsequently, the toxin is administered at varying doses, such as 0.1 µg to 1 mg, intravenously to LNCaP bearing animals to demonstrate that an enhanced anti-tumor effect is observed at higher, less toxic doses of toxin.

EXAMPLE 7

Determination of Proaerolysin Antigenicity

This example provides methods to determine if the modified proaerolysin peptides disclosed herein are antigenic. In addition, methods to reduce potential antigenicity are disclosed.

As described in the Examples above, intratumoral injection of PSA-PA1 (SEQ ID NO: 4) demonstrates the usefulness of the toxin as therapy for localized prostate cancer via intraprostatic injection. However, such a therapy can also be administered by other routes, such as intravenous (iv), intramuscularly, orally, etc., as a systemic therapy for metastatic prostate cancer. However, systemic administration of the variant PA peptides disclosed herein may result in the development of a neutralizing antibody response that would limit repeat dosing.

The kinetics and magnitude of the antibody response to any of the PA variants disclosed herein can be determined as follows. For example, the antigenic response to PSA-PA1 (SEQ ID NO: 4) can be determined in immunocompetent mice, to develop a dosing regimen that can be used in a immunocompetent human. Immunocompetent mice (C57-BL6) are administered iv doses of PSA-PA1 (SEQ ID NO: 5) both daily×5 and weekly×3 at a dose range from 0.1 µg to 5 µg. Mice are sacrificed at varying intervals (e.g. following single dose, following multiple doses) and serum obtained. An ELISA-based assay can be used to detect presence of anti-proaerolysin antibodies. In this assay, a defined quantity of proaerolysin is fixed to the polystyrene surface in 96-well plates. Following adequate blocking with bovine serum albumin (BSA), serum from mice exposed to proaerolysin is added to the wells at varying dilutions. After a defined incubation time, wells are washed, and alkaline phosphatase linked goat-anti-mouse secondary antibody is added, followed by substrate. The amount of antibody present is determined by measuring absorbance in a spectrophotometer, which permits determination of the time course and magnitude of the antibody response by varying schedules and doses of iv PSA-PA1.

To decrease antigenicity of proaerolysin, the native binding domain can be functionally deleted and replaced, for example with LHRH, as described in Example 6. The antigenicity of such peptides can be determined following exposure to varying schedules of LHRH-proaerolysin proteins which lack portions of the native binding domain using the methods described above. Another method that can be used to allow continued treatment with prostate-specific protease activated toxins is to use alternative lytic toxins with non-overlapping antigenicity (see Example 10). One example is to use a modified, structurally related bacterial toxin such as *Clostridium septicum* alpha toxin that can also be activated by a prostate-specific protease, such as PSA, but would not be recognized or neutralized by antibodies that recognize PA (see Example 10). Another example is to use a pore-forming toxin produced by human tissues, such as human perforin produced by cytolytic human T cells. Modified performs in which the wild type activation sequence is replaced by peptides that are substrates for prostate-specific proteases, such as PSA, can be administered and not produce an antibody response because the proteins are of human origin.

In addition, methods are provided to determine whether the antibody produced can neutralize the cytolytic properties of aerolysin. A disclosed modified PA (such as SEQ ID NOS: 4, 24 and 25) is incubated with PSA to activate the toxin. Activated toxin is incubated with antibody containing serum at varying doses. Washed RBC's are added to determine degree of hemolysis versus control (non-serum exposed toxin) as described above in Example 2.

In addition, PSA-producing tumor bearing animals can be inoculated twice with PSA-activated proaerolysin toxins, then rechallenged with a lethal dose of toxin (see Example 4) to determine if antibody neutralizes toxicity in vivo. Subsequently, the anti-tumor response following intratumoral injection of vaccinated animals is assessed, to determine if antibodies neutralize toxin when injected intratumorally.

EXAMPLE 8

Induction of a Systemic Immunostimulatory Response

This example provides methods that can be used to demonstrate that proaerolysin-mediated cell lysis produces a systemic immunostimulatory effect. Such a systematic immunostimulatory effect resulting from an intraprostatic administration of the toxins disclosed herein would provide both local therapy for prostate cancer within the prostate gland, while simultaneously induce a systemic antitumor effect against occult micrometastatic disease. Alternatively or in addition, subjects can be vaccinated with modified proaerolysin-lysed prostate cancer cells in the presence or absence of cytokines, such as GMCSF, to treat recurrent or initial metastatic disease.

Administration of Prostate Tumor Cells Lysed with Modified Proaerolysin

To demonstrate that modified proaerolysin treated cells stimulate a systemic immune response in a subject, the following methods can be used. Briefly, subjects (such as immunocompetent mice or a human subject having prostate cancer) are administered prostate tumor cells (such as TC2 mouse prostate tumor cells, prostate cancer cells obtained from the subject having prostate cancer, and/or human prostate cancer cell lines for administration to patients) which have been lysed with one or more modified proaerolysin molecules disclosed herein. To determine whether a systemic immune response occurs, mice that have been administered lysed prostate cancer cells can be rechallenged with the same cells and growth of these inoculated tumor cells measured. For example, C57-BL6 mice are subcutaneously injected with proaerolysin lysed TC2 cells. To accomplish this, $10^7$ TC2 cells are lysed by incubation with proaerolysin for 1 hour at 37° C. in sterile phosphate buffered saline (PBS). Animals are administered two weekly injections of this cell lysate to stimulate an immune response to the TC2 cells. Animals are subsequently rechallenged with a subcutaneous injection of TC2 cancer cells one week after the second lysate inoculation. TC2 is a mouse prostate cancer cell line derived from cancerous tissue isolated from a TRAMP mouse (Foster et al., *Cancer Res.* 57:3325-30, 1997). Control subjects will receive a similar number of cells that have been lysed by freezing and thawing, or that have been treated with radiation to induce apoptosis. Another control group will receive only the modified proaerolysin peptide. Tumor growth is compared between the groups using the methods described in Example 5.

For human subjects, prostate cancer cells can be obtained from patient at time of prostatectomy or biopsy or human prostate cancer cell lines can be used. Examples of human prostate cancer cell lines include PSA-producing LNCaP (such as ATTC Nos. CRL-1740 and CRL-10995) or CWR22R (ATCC No. CRL-2505 and Nagabhushan et al., *Cancer Res.* 56(13):3042-6, 1996) cells, or PSA non-producing PC-3 (ATCC No. CRL-1435) and DU 145 (ATCC No. HTB-81). Approximately $10^7$-$10^8$ cells from either source (patient or cell lines) are incubated with 1 μg of PA (wild-type or variant) for 1 hour at 37° C. in sterile PBS. The resulting lysate is mixed thoroughly using vigorous pipetting, and suspension is administered to a subject via subcutaneous injection of ~0.5 ml. Patients can be treated weekly for 3 doses. Patients are closely monitored with weekly physical exams. Immune response to subcutaneous PA can be monitored by assaying presence of antibodies to PSA, PSMA, and hK2, and assaying for B and T cell response using methodology previously described (Simons et al. *Cancer Res.* 59:5160-8, 1999).

Alternatively, or in addition, prostate cancer cells from a patient or prostate cancer cell lines engineered to express immunostimulatory proteins (such as GM-CSF) are incubated with PA (wild-type or variant) and used to produce the lysate (for example see Simons et al. *Cancer Res.* 59:5160-8, 1999). PA-lysed prostate cancer cells can be co-administered with irradiated prostate cancer cells producing immunostimulatory molecules. Irradiation induces cells to undergo apoptosis. The combination of cells killed by cytolysis and cells killed by induction of apoptosis is expected to produce superior immunostimulatory effects (Sauter et al. *J. Exp. Med.* 191:423-33, 2000). In one example, a subject is co-administered PA-lysed prostate cancer cells mixed with immunostimulatory protein. In another example, PA-lysed prostate cancer cells are administered subcutaneously, and an immunostimulatory protein, such as GM-CSF, interleukins, interferons, G-CSF (Dranoff et al. *Proc. Natl. Acad. Sci. USA* 90:3539-43, 1993) is systemically administered.

Intraprostatic Administration of Modified Proaerolysin

Another method that can be used to stimulate a systemic immune response in a subject having prostate cancer is to administer the modified proaerolysin toxins disclosed herein directly into the prostate gland of the subject. For example, modified proaerolysin toxins can be administered directly into the prostate gland (or the tumor itself) of a human subject having a prostate tumor, or into transgenic ProHA mice followed by adoptive transfer of hemagglutinin (HA) primed T cells. It is expected that cytolysis following intraprostatic injection of modified proaerolysin toxins will provoke immune response to HA in the prostate gland of ProHA mice, or to prostate tumor antigens in humans. ProHA transgenic mice express the influenza protein HA under the control of the prostate-restricted promoter probasin. ProHA mice express HA only in the prostate gland. In this system, specific CD4 and CD8 T cells from separate donor mice are primed by exposure to HA and then adoptively transferred into the HA transgenic animal.

Subjects are administered a sublethal intraprostatic dose of modified proaerolysin (for instance determined using the methods described in Example 4). Because ProHA mice do not produce PSA or an enzymatically equivalent homolog, wild type aerolysin is used. However in humans, one or more of the disclosed modified proaerolysin toxins are administered. Twenty-four hours after the intraprostatic injection, some mice are sacrificed and prostates removed and analyzed for degree of necrosis. A second group of injected mice will receive HA specific CD4 and CD8 T cells, which have been harvested from TCR transgenic donors inoculated with $10^9$ pfu of recombinant hemagglutinin expressing vaccinia virus as previously described (Staveley-O'Carroll et al., *Proc. Natl. Acad. Sci. USA* 95:1178-83, 1998). These T cells are Thy 1.1+ and are transferred into the ProHA mice which are Thy1.2+. Four days after adoptive transfer into the proaerolysin treated ProHA mice, recipient mice are sacrificed, and the spleen, axillary (irrelevant) and prostate draining nodes dissected, dissociated and washed.

To assess activation of specific T cells, the following assays can be performed: One million isolated cells are stained using a Phycoerythrin labeled anti Thy1.1 antibody and cychrome labeled antiCD4 or CD8 antibody (Pharmingen, San Diego, Calif.). Isolated cells are analyzed using FacsScan (Becton Dickinson). The index of expansion of HA specific T cells is calculated by dividing the percentage of clonotypic (Thy 1.1+) cells in the ProHA treated animals by the percentage of clonotypic cells in an identical tissue location in untreated ProHA controls. In addition, the ratio of percentage of clonotypic cells in the prostate draining versus irrelevant lymph nodes provides an index of prostate specific proliferation following PA treatment. In a another assay, antigen-specific proliferation is measured as described previously (Adler et al. *J. Exp. Med.* 187:1555-64, 1998). Briefly, pooled lymphocytes or splenocytes are incubated with HA class II peptide (CD4 cell specific proliferation) or HA class I peptide (CD8 cell specific proliferation). Cells are cultured for three days then pulsed overnight with tritiated thymidine followed by harvest and determination of counts. Increased incorporated counts over control signifies specific T cell activation.

The prostate glands from the PA treated ProHA mice that received HA specific Thy1.1 T cells are analyzed as follows. Fixed prostate sections from treated mice are stained with biotinylated Thy1.1 antibody (Pharmingen) and counterstained with streptavidin peroxidase using standard immunohistochemical procedures. To determine extent of stimulation, the degree of positive staining is compared to saline treated controls.

To assess whether intraprostatic proaerolysin can effect subsequent tumor development, growth or pattern of spread, the following methods can be used. Proaerolysin (or the modified proaerolysin peptides disclosed herein) can be injected into prostate of TRAMP mice at various time points in the life cycle of the animal (pre-pubescent, post pubescent prior to metastatic disease, with metastatic disease). Anesthetized animals are injected intraprostatically under sterile conditions. At various time points following intraprostatic inoculation, animals are sacrificed and necropsy performed to evaluate extent of tumor. Prostate glands are removed and immunohistochemical analysis performed to assess presence of precursor lesions and overt prostate cancer. Similarly, prepubescent TRAMP animals can be twice subcutaneously administered proaerolysin lysed TC2 cells or proaerolysin lysed primary tumors removed from late stage cancer bearing TRAMP mice. These animals are followed and sacrificed at defined time points to assess time course and magnitude of tumor development compared to controls.

A similar approach can be used to administer modified PA to patients with localized prostate cancer. Such intraprostatic modified PA therapy can be used as initial treatment for localized prostate cancer either alone, or in combination with radiation (external beam or brachytherapy) and/or androgen ablation therapy. The intraprostatic modified PA therapy can also be administered to patients who have failed radiation therapy and are suspected to only have a local recurrence of prostate cancer within the prostate gland. The intraprostatic modified PA therapy can also be given to patients with localized and metastatic prostate cancer to treat the localized cancer directly and to treat the metastatic cancer via stimulation of a systemic anti-tumor immune response.

To produce the intraprostatic modified PA therapy, modified PA is injected into the prostate gland of patients according to a predefined template similar to that used to administer intraprostatic brachytherapy. The techniques and equipment required for intraprostatic administration are also similar to those used for brachytherapy and have been previously described (Deweese et al., *Cancer Res.* 61:7464-72, 2001). To determine the appropriate dose to be administered intraprostatically, a dose finding clinical trial is performed. Patients will receive multiple injections (20-80) at predefined sites to encompass the entire prostate gland. The total dose of administered modified PA will range from about 0.1-1.0 mg, and not more than 10 mg total. The dose per injection will be determined by dividing total dose by total number of injections. Patients are treated as in patients and monitored in the hospital for 48 hours post injection. Subsequently, patients will be examined weekly for signs of toxicity. MRI of the prostate can be used to monitor direct treatment effect on prostatic size. Immune response to intraprostatic PA will be monitored as previously described (Simons et al. *Cancer Res.* 59:5160-8, 1999).

EXAMPLE 9

Additional PSA Cleavage Sites

Additional PSA cleavage sites are known, based on the PSA-cleavage map of human seminal proteins semenogelin I and II, and a cellulose membrane based assay (see Table 2 and Denmeade et al., *Cancer Res.*, 57:4924-30, 1997). The PSA-cleavage sites shown in Table 2 can substitute for the wild-type furin protease activation site of proaerolysin (amino acids 427-432 of SEQ ID NO: 2), using the methods described in Example 1. Briefly, recombinant PCR can be used to replace the furin site of PA with a PSA-specific cleavage site, such as those shown in Tables 1 and 2. The variant PA sequence is subcloned into pMMB66HE for expression in *E. coli*. Recombinant clones are transferred into a protease deficient strain of *A. salmonicida*, and the resulting variant proaerolysin protein purified by hydroxyapatite chromatography and ion exchange chromatography.

TABLE 2

Kinetics of PSA hydrolysis.*

| PSA Substrate (SEQ ID NO) | $K_m$ (uM) | $K_{cat}$ (S$^{-1}$) | $K_{cat}/K_m$ (s$^{-1}$M$^{-1}$) |
|---|---|---|---|
| KGISSQY (15) | 160 | 0.043 | 270 |
| SRKSQQY (16) | 90 | 0.023 | 260 |
| ATKSKQH (17) | 1310 | 0.0091 | 6.9 |
| KGLSSQC (18) | 300 | 0.0017 | 5.6 |
| LGGSSQL (19) | 900 | 0.0037 | 4.1 |
| EHSSKLQ (20) | 1165 | 0.012 | 10.6 |
| HSSKLQ (5) | 470 | 0.011 | 23.6 |
| SKLQ (21) | 813 | 0.020 | 24.6 |

*Peptides were fluorescently labeled (aminomethyl coumarin). Assays were performed in 50 mM Tris, 0.1 M NaCl, pH 7.8.

The sequences shown in Table 2 include substrates that were efficiently but not specifically hydrolyzed by PSA (KGISSQY; SEQ ID NO: 15) and SRKSQQY; SEQ ID NO: 16), and those that were not efficient, but were specifically hydrolyzed by PSA (ATKSKQH; SEQ ID NO: 17 and LGGSSQL; SEQ ID NO: 19). The characteristics of these modified toxins can be compared to PSA-PA1 containing the HSSKLQ (SEQ ID NO: 5) sequence. As a control, a modified toxin is produced in which the activation site is completely deleted (EX-PA).

These purified toxins are screened for PSA hydrolysis using the hemolysis assay described in Example 3. Wild type proaerolysin is not activated or cytolytic to erythrocytes. Activation of proaerolysin by proteases, however, results in rapid hemolysis. Briefly, to assay PSA activation, varying concentrations of purified variant PA toxins are incubated with PSA for 1 hour, washed, and serum free red blood cells (RBC's) (2% v/v) added. After another 1 hour, incubation mixtures are centrifuged and absorbance of the supernatant at 540 nm determined. Minimal concentration of modified toxin required to lyse 50% of RBC's is determined to rank toxins on basis of efficiency of PSA hydrolysis.

To determine both PSA-activation and specificity of activation, cytotoxicity assays are performed by exposing purified PSA-proaerolysin toxins to PSA-producing (LNCaP) and non-producing cancer cell lines (TSU) in vitro, using the methods described in Example 2. The concentration required to kill 50% of cells (IC$_{50}$) can be determined for each variant PA toxin against both LNCaP and TSU lines. The fold-difference in cytotoxicity is used to rank PSA-activated toxins on basis of specificity.

Variant PA toxins can also be screened in vivo for antitumoral activity by intratumoral injection into PSA-producing LNCaP xenografts in nude mice, using the methods described in Example 5. As described above in Example 5, intratumoral injection of the PSA-PA1 toxin reduces the tumor within 48 hours. In contrast, wild type proaerolysin, which is more efficiently activated by both PSA-producing and non-producing cell lines in vitro, had minimal effect against the LNCaP xenografts. This indicates that the kinetics of toxin activation may be important in the overall antitumor effect. PSA-PA1 is activated more specifically by PSA, but the kinetics of activation are slower than the wild type toxin. This may allow PSA-PA1 to distribute more widely throughout the tumor.

Therefore, better PSA substrates in the activation site, paradoxically may result in decreased overall antitumor effect in vivo.

To assess distribution of PSA-activated proaerolysin versus wild type PA intratumorally or into normal tissue, fluorescently labeled (such as FITC) PSA-PA1 and PA proteins can be used. PSA-producing LNCAP xenografts are injected with the fluorescently labeled PSA-PA1 and PA. At 24 hours following intratumoral injection, tumors are harvested, fixed and sectioned for microscopic analyses. Fluorescently labeled proaerolysin proteins that have inserted into cell membranes are retained throughout the fixation process. These slides are then analyzed using a fluorescence microscope equipped with the appropriate filter set to determine degree of distribution of the proaerolysin toxins throughout the tumor specimen.

Subsequently, variant PA toxins are injected into LNCaP xenografts and antitumor response assessed after 48 hours by tumor measurement, using the methods described in Example 5. The variant PA toxins are ranked on the basis of in vivo antitumor effect following intratumoral injection.

In addition, variant PA toxins can be tested for overall systemic toxicity by determining the dose that kills 100% of mice (i.e. $LD_{100}$) following a single intravenous injection, using the methods described in Example 4.

Using these methods, PSA-activated variant PA toxins which are most efficiently and specifically activated by PSA, are the least toxic systemically and produce the most pronounced antitumor effect in vivo, are identified. Such PSA-activated variant PA toxins can also be modified using the methods described in Example 6.

EXAMPLE 10

Reduction of Antigenicity of PSA-Activated Modified Proaerolysin Toxin

This example describes additional methods than can be used to produce and characterize antigenicity and anti-tumor efficacy of other modified pore forming protease activated protoxins.

One method to overcome the potential antigenicity of the disclosed variant PA toxins is to sequentially administer structurally related protoxins that are similarly activated by PSA, but which are not recognized by proaerolysin antibodies. Examples of such protoxins include, but are not limited to, *Clostridium septicum* alpha toxin (Ballard et al., *Infect. Immun.* 63:340-4, 1995; Gordon et al. *J. Biol. Chem.* 274: 27274-80, 1999; Genbank Accession No. S75954), *Bacillus Thuringiensis* delta-toxin (Genbank Accession No. D00117), and human perforin (Genbank Accession No. NM005041). While mechanistically similar to aerolysin, these protoxins have different peptide sequences such that antibodies specific to proaerolysin would not recognize them. These protoxins have been cloned and recombinant forms produced (Imagawa et al., *FEMS. Microbiol. Lett.* 17:287-92, 1994; Meza et al. *FEMS Microbiol. Lett.* 145:333-9, 1996).

These protoxins, like proaerolysin, contain a C-terminal inhibitory peptide that must be removed by proteolytic cleavage for activation to occur. The activation site within each of these protein toxins has been defined. For *Clostridium septicum* alpha toxin, the activation site is a furin cleavage site (Gordon et al., *Infect. Immun.* 65:4130-4, 1997). The activation site of *Bacillus Thuringiensis* delta-toxin is cleaved by proteases in the midgut of certain insects (Miranda et al., *Insect Biochem. Mol. Biol.* 31:1155-63, 2001). For human perforin, the activation sequence has been defined but the activating protease has not yet been identified (Uellner et al., *EMBO J.* 16:7287-96, 1997).

The activation site of each of these protoxins can be modified to contain a prostate-specific protease cleavage site (such as the PSA cleavage sites shown in Tables 1-2) using the methods described in Example 1. If desired, the native protoxin binding domain can be functionally deleted and replaced with a prostate-tissue specific binding domain, using the methods described in Example 6. Alternatively, the activation site is not modified, but the binding domain is functionally deleted and replaced with a prostate-tissue specific binding domain, using the methods described in Example 6. These modified protoxins are assayed for protease activation, for example using the RBC hemolysis assay (Example 3), for in vitro activity against PSA-producing and non-PSA producing cell lines (Example 2) and stability in human serum (Example 3). If these toxins are specifically and efficiently activated by PSA, then they are tested in vivo for activity against PSA-producing xenografts using the methods described in Example 5. In addition, kinetics and magnitude of antibody production will be determined using methods described in Example 7. Serum from animals treated with each toxin is screened for cross reactivity with each of the other members of the toxin family to determine degree of cross-recognition.

Another method for reducing the systemic immune response is to administer immunosuppressive therapies. Examples of immunosuppressive therapies include, but are not limited to, systemic or topical corticosteroids (Suga et al., *Ann. Thorac. Surg.* 73:1092-7, 2002), cyclosporin A (Fang et al., *Hum. Gene Ther.* 6:1039-44, 1995), cyclophosphamide (Smith et al., *Gene Ther.* 3:496-502, 1996), deoxyspergualin (Kaplan et al., *Hum. Gene Ther.* 8:1095-1104, 1997) and antibodies to T and/or B cells [e.g. anti-CD40 ligand, anti CD4 antibodies, anti-CD20 antibody (Rituximab)] (Manning et al., *Hum. Gene Ther.* 9:477-85, 1998). Such agents can be administered before, during, or subsequent to administration of modified PA molecules and/or cell lysates produced by incubation with PA (wild-type or variant).

EXAMPLE 11

Production of Sequence Variants

Disclosed herein are agents and methods for treating prostate cancer by administration of a modified proaerolysin peptide which includes a prostate-specific protease cleavage site. It is understood by those skilled in the art that use of other proaerolysin, PSA, LHRH, and PSMA sequences (such as polymorphisms, fragments, or variants) can be used to practice the methods of the present disclosure, as long as the distinctive functional characteristics of the sequence are retained. For example, proaerolysin variants can be used to practice the methods disclosed herein if they retain their ability to be activated by a prostate-specific protease and form pores in cell membranes, resulting in cell death. This activity can readily be determined using the assays disclosed herein, for example those described in EXAMPLES 2-5. In yet other embodiments, modified proaerolysin molecules have the characteristic of specifically lysing PSA-producing cells (for example, lyse PSA-producing cells to a greater extent than non-PSA producing cells).

This disclosure facilitates the use of DNA molecules, and thereby proteins, derived from a native protein but which vary in their precise nucleotide or amino acid sequence from the native sequence. Such variants can be obtained through standard molecular biology laboratory techniques and the sequence information disclosed herein.

DNA molecules and nucleotide sequences derived from a native DNA molecule can also be defined as DNA sequences which hybridize under stringent conditions to the DNA sequences disclosed, or fragments thereof. Hybridization conditions resulting in particular degrees of stringency vary depending upon the nature of the hybridization method and the composition and length of the hybridizing DNA used. Generally, the temperature of hybridization and the ionic strength (especially the $Na^+$ concentration) of the hybridization buffer determines hybridization stringency. Calculations regarding hybridization conditions required for attaining particular amounts of stringency are discussed by Sambrook et al. (Molecular Cloning: A Laboratory Manual, Cold Spring Harbor, N.Y., 1989, Chapters 9 and 11), herein incorporated by reference. Hybridization with a target probe labeled with $[^{32}P]$-dCTP is generally carried out in a solution of high ionic strength such as 6×SSC at a temperature that is about 5-25° C. below the melting temperature, $T_m$. An example of stringent conditions is a salt concentration of at least about 0.01 to 1.0 M Na ion concentration (or other salts) at pH 7.0 to 8.3 and a temperature of at least about 30° C. for short probes (e.g. 10 to 50 nucleotides). Stringent conditions can also be achieved with the addition of destabilizing agents such as formamide. For example, conditions of 5×SSPE (750 mM NaCl, 50 mM Na phosphate, 5 mM EDTA, pH 7.4) at 25-30° C. are suitable for allele-specific probe hybridizations.

The degeneracy of the genetic code further widens the scope of the present disclosure as it enables major variations in the nucleotide sequence of a DNA molecule while maintaining the amino acid sequence of the encoded protein. For example, the amino acid Ala is encoded by the nucleotide codon triplet GCT, GCG, GCC and GCA. Thus, the nucleotide sequence could be changed without affecting the amino acid composition of the encoded protein or the characteristics of the protein. Based upon the degeneracy of the genetic code, variant DNA molecules may be derived from a cDNA molecule using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are also comprehended by this disclosure.

PA variants, fragments, fusions, and polymorphisms will retain the ability to lyse PSA-producing cells, as determined using the assays disclosed herein (for example, see Examples 2 and 5). Variants and fragments of a the disclosed sequences retain at least 70%, 80%, 85%, 90%, 95%, 98%, or greater sequence identity to a protein amino acid sequence and maintain the functional activity of the protein as understood by those in skilled in the art.

EXAMPLE 12

Recombinant Expression of Proteins

With publicly available cDNA and corresponding amino acid sequences, as well as the disclosure herein of PA variants, fragments and fusions, the expression and purification of any protein by standard laboratory techniques is enabled. The purified protein can be used for patient therapy. One skilled in the art will understand that the disclosed modified PA toxins can be produced in any cell or organism of interest, and purified prior to administration to a subject.

Methods for producing recombinant proteins are well known in the art. Therefore, the scope of this disclosure includes recombinant expression of any protein. For example, see U.S. Pat. No. 5,342,764 to Johnson et al.; U.S. Pat. No. 5,846,819 to Pausch et al.; U.S. Pat. No. 5,876,969 to Fleer et al. and Sambrook et al. (Molecular Cloning: A Laboratory Manual, Cold Spring Harbor, N.Y., 1989, Ch. 17, herein incorporated by reference).

EXAMPLE 13

Peptide Modifications

Modified PA proteins which are activated by a prostate-specific protease, such as PSA, can be modified using a variety of chemical techniques to produce derivatives having essentially the same activity as the unmodified peptides, and optionally having other desirable properties (such as reduced antigenicity). For example, carboxylic acid groups of the peptide, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chain can be converted to $C_1$-$C_{16}$ alkoxy or to a $C_1$-$C_{16}$ ester using well-recognized techniques. Phenyl and phenolic rings of the peptide side chain can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides disclosed herein to select and provide conformational constraints to the structure that result in enhanced stability. For example, a carboxyl-terminal or amino-terminal cysteine residue can be added to the peptide, so that when oxidized the peptide will contain a disulfide bond, generating a cyclic peptide. Other peptide cyclizing methods include the formation of thioethers and carboxyl- and amino-terminal amides and esters.

To maintain a functional peptide, particular peptide variants will differ by only a small number of amino acids from a peptide. Such variants can have deletions (for example of 1-3 or more amino acids), insertions (for example of 1-3 or more residues), or substitutions that do not interfere with the desired activity of the peptide. Substitutional variants are those in which at least one residue in the amino acid sequence has been removed and a different residue inserted in its place. In particular embodiments, such variants have amino acid substitutions of single residues, for example 1, 3, 5 or even 10 substitutions in a protein.

Peptidomimetic and organomimetic embodiments are also disclosed herein, whereby the three-dimensional arrangement of the chemical constituents of such peptido- and organomimetics mimic the three-dimensional arrangement of the peptide backbone and component amino acid sidechains in the peptide, resulting in such peptido- and organomimetics of a modified PA toxin which has the ability to lyse PSA-producing cells. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, Pharmaceutical Biotechnology, Interpharm Press: Buffalo Grove, Ill., pp. 165-174 and Principles of Pharmacology (ed. Munson, 1995), chapter 102 for a description of techniques used in CADD.

EXAMPLE 14

Methods for Expressing Modified Proaerolysin Peptides

As an alternative to (or in addition to) administration of a modified proaerolysin peptide to treat prostate cancer, long term or systemic treatment (for example to treat or prevent metastasis of the tumor) can be achieved by expressing the disclosed modified proaerolysin toxins in vivo.

The present disclosure provides methods of expressing a modified proaerolysin peptide in a cell or tissue in vivo. In one example, transfection of the cell or tissue occurs in vitro. In this example, the cell or tissue (such as a graft) is removed from a subject and then transfected with an expression vector containing a cDNA encoding the protein of interest. The transfected cells will produce functional protein and can be reintroduced into the subject. In another example, a nucleic acid encoding the protein of interest is administered to a subject directly (such as intravenous, intratumor or intraprostate), and transfection occurs in vivo.

The modified proaerolysin peptides and methods disclosed herein can be used to treat a subject with a prostate tumor. Such a method would decrease the volume of the tumor, and in some embodiments, prevent or treat metastasis of the prostate tumor.

The scientific and medical procedures required for human cell transfection are now routine. The public availability of proaerolysin, binding domains, and prostate-specific protease protein and cDNA sequences allows the development of human (and other mammals) in vivo gene expression based upon these procedures. In addition, particular variant proaerolysin molecules are disclosed herein. Immunotherapy of melanoma patients using genetically engineered tumor-infiltrating lymphocytes (TILs) has been reported by Rosenberg et al. (*N. Engl. J. Med.* 323:570-8, 1990). In that study, a retrovirus vector was used to introduce a gene for neomycin resistance into TILs. A similar approach can be used to introduce a modified proaerolysin peptide cDNA into a subject having a prostate cancer.

A general strategy for transferring genes into donor cells is disclosed in U.S. Pat. No. 5,529,774, incorporated by reference. Generally, a gene encoding a protein having therapeutically desired effects is cloned into a viral expression vector, and that vector is then introduced into the target organism. The virus infects the cells, and produces the protein sequence in vivo, where it has its desired therapeutic effect (Zabner et al. *Cell* 75:207-16, 1993).

It may only be necessary to introduce the DNA or protein elements into certain cells or tissues. For example, if a subject only has a prostate tumor, introducing the protein or DNA into only the prostate (or tumor) may be sufficient. However, in some instances, it may be more therapeutically effective and simple to treat all of a subject's cells, or more broadly disseminate the vector, for example by intravascular (i.v.) or oral administration. For example, if a subject has a prostate tumor that has metastasized, introducing the protein or DNA systemically may be necessary.

The nucleic acid sequence encoding at least one therapeutic agent, such as a modified proaerolysin toxin, is under the control of a suitable promoter. Suitable promoters which can be used include, but are not limited to, the gene's native promoter, retroviral LTR promoter, or adenoviral promoters, such as the adenoviral major late promoter; the CMV promoter; the RSV promoter; inducible promoters, such as the MMTV promoter; the metallothionein promoter; heat shock promoters; the albumin promoter; the histone promoter; the α-actin promoter; TK promoters; B19 parvovirus promoters; and the ApoAI promoter. In one example, the promoter is a prostate-specific promoter, such as a probasin promoter. However the disclosure is not limited to specific foreign genes or promoters.

The recombinant nucleic acid can be administered to the subject by any method which allows the recombinant nucleic acid to reach the appropriate cells. These methods include injection, infusion, deposition, implantation, or topical administration. Injections can be intradermal or subcutaneous. The recombinant nucleic acid can be delivered as part of a viral vector, such as avipox viruses, recombinant vaccinia virus, replication-deficient adenovirus strains or poliovirus, or as a non-infectious form such as naked DNA or liposome encapsulated DNA, as further described in EXAMPLE 15.

EXAMPLE 15

Viral Vectors for in vivo Gene Expression

Adenoviral vectors include essentially the complete adenoviral genome (Shenk et al., *Curr. Top. Microbiol. Immunol.* 111:1-39, 1984). Alternatively, the adenoviral vector is a modified adenoviral vector in which at least a portion of the adenoviral genome has been deleted. In one example, the vector includes an adenoviral 5' ITR; an adenoviral 3' ITR; an adenoviral encapsidation signal; a DNA sequence encoding a therapeutic agent; and a promoter for expressing the DNA sequence encoding a therapeutic agent. The vector is free of at least the majority of adenoviral E1 and E3 DNA sequences, but is not necessarily free of all of the E2 and E4 DNA sequences, and DNA sequences encoding adenoviral proteins transcribed by the adenoviral major late promoter. In another example, the vector is an adeno-associated virus (AAV) such as described in U.S. Pat. No. 4,797,368 (Carter et al.) and in McLaughlin et al. (*J. Virol.* 62:1963-73, 1988) and AAV type 4 (Chiorini et al. *J. Virol.* 71:6823-33, 1997) and AAV type 5 (Chiorini et al. *J. Virol.* 73:1309-19, 1999).

Such a vector can be constructed according to standard techniques, using a shuttle plasmid which contains, beginning at the 5' end, an adenoviral 5' ITR, an adenoviral encapsidation signal, and an E1a enhancer sequence; a promoter (which may be an adenoviral promoter or a foreign promoter); a tripartite leader sequence, a multiple cloning site (which may be as herein described); a poly A signal; and a DNA segment which corresponds to a segment of the adenoviral genome. The DNA segment serves as a substrate for homologous recombination with a modified or mutated adenovirus, and may encompass, for example, a segment of the adenovirus 5' genome no longer than from base 3329 to base 6246. The plasmid can also include a selectable marker and an origin of replication. The origin of replication may be a bacterial origin of replication. A desired DNA sequence encoding a therapeutic agent can be inserted into the multiple cloning site of the plasmid.

Examples of vectors which can be used to practice the methods disclosed herein include, but are not limited to, those disclosed in: WO 95/27512 to Woo et al.; WO 01/127303 to Walsh et al.; U.S. Pat. No. 6,221,349 to Couto et al.; U.S. Pat. No. 6,093,392 to High et al.

EXAMPLE 16

Generation and Expression of Fusion Proteins

Methods for making fusion proteins are well known to those skilled in the art. For example U.S. Pat. No. 6,057,133 to Bauer et al. (herein incorporated by reference) discloses methods for making fusion molecules composed of human interleukin-3 (hIL-3) variant or mutant proteins functionally joined to a second colony stimulating factor, cytokine, lymphokine, interleukin, hematopoietic growth factor or IL-3 variant. U.S. Pat. No. 6,072,041 to Davis et al. (herein incorporated by reference) discloses the generation of fusion proteins comprising a single chain Fv molecule directed against a transcytotic receptor covalently linked to a therapeutic protein.

Similar methods can be used to generate fusion proteins comprising PA (or variants, fragments, etc. thereof) linked to other amino acid sequences, such as a prostate specific binding domain (for example LHRH or an antibody). Linker regions can be used to space the two portions of the protein from each other and to provide flexibility between them. The linker region is generally a polypeptide of between 1 and 500 amino acids in length, for example less than 30 amino acids in length. The linker joining the two molecules can be designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4) provide steric separation of the two regions. Typically surface amino acids in flexible protein regions include Gly, Asn and Ser. Other neutral amino acids, such as Thr and Ala, can also be used in the linker sequence. Additional amino acids can be included in the linker due to the addition of unique restriction sites in the linker sequence to facilitate construction of the fusions. Other moieties can also be included, as desired. These can include a binding region, such as avidin or an epitope, such as a polyhistadine tag, which can be useful for purification and processing of the fusion protein. In addition, detectable markers can be attached to the fusion protein, so that the traffic of the fusion protein through a body or cell can be monitored conveniently. Such markers include radionuclides, enzymes, fluorophores, and the like.

Fusing of the nucleic acid sequences of PA (or variant, fragment etc. thereof), with the nucleic acid sequence of another protein (or variant, fragment etc. thereof), can be accomplished by the use of intermediate vectors. Alternatively, one gene can be cloned directly into a vector containing the other gene. Linkers and adapters can be used for joining the nucleic acid sequences, as well as replacing lost sequences, where a restriction site was internal to the region of interest. Genetic material (DNA) encoding one polypeptide, peptide linker, and the other polypeptide is inserted into a suitable expression vector which is used to transform prokaryotic or eukaryotic cells, for example bacteria, yeast, insect cells or mammalian cells. The transformed organism is grown and the protein isolated by standard techniques, for example by using a detectable marker such as nickel-chelate affinity chromatography, if a polyhistadine tag is used. The resulting product is therefore a new protein, a fusion protein, which has modified PA joined by a linker region to a second protein. To confirm that the fusion protein is expressed, the purified protein is subjected to electrophoresis in SDS-polyacrylamide gels, and transferred onto nitrocellulose membrane filters using established methods. The protein products can be identified by Western blot analysis using antibodies directed against the individual components, i.e., polyhistadine tag and PA.

EXAMPLE 17

Pharmaceutical Compositions and Modes of Administration

The pharmaceutically effective carriers useful herein are conventional. Remington's Pharmaceutical Sciences, by Martin, Mack Publishing Co., Easton, Pa., 15th Edition (1975), describes compositions and formulations suitable for pharmaceutical delivery.

Administration of Peptides

In an embodiment in which a modified PA toxin, such as SEQ ID NOS: 4, 24 and 25, is administered to a subject, the protein is delivered by any route used by those in the art. Examples include, but are not limited to: intravenously, intratumorally, orally, intraprostatically, intramuscularly, subcutaneous injection, transdermal, etc. The present disclosure also provides pharmaceutical compositions which include a therapeutically effective amount of a modified PA toxin alone or with a pharmaceutically acceptable carrier. Furthermore, the pharmaceutical compositions or methods of treatment can be administered in combination (or separately) with one or more other therapeutic treatments. Examples of other therapeutics include, but are not limited to anti-tumor agents, cell lysates (such as those generated by incubation with a modified PA toxin), non-lysed cells (such as those that have been killed by radiation), immunosuppressants (such as Rituximab, steroids), and/or cytokines (such as GM-CSF). Embodiments of the disclosure including medicaments can be prepared with conventional pharmaceutically acceptable carriers, adjuvants and counterions as would be known to those of skill in the art.

The modified PA toxin can be administered in combination with at least one, for example one or more pharmaceutically effective carriers, such as a pharmaceutically and physiologically acceptable fluid. Examples of pharmaceutically effective carriers include, but are not limited to water, physiological saline, balanced salt solutions, aqueous dextrose, sesame oil, glycerol, ethanol, combinations thereof, or the like, as a vehicle. The carrier and composition can be sterile, and the formulation suits the mode of administration. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The composition can be a liquid solution, suspension, emulsion, tablet, pill, capsule, sustained release formulation, or powder. For solid compositions (e.g., powder, pill, tablet, or capsule forms), conventional non-toxic solid carriers can include, for example, pharmaceutical grades of mannitol, lactose, starch, sodium saccharine, cellulose, magnesium carbonate, or magnesium stearate. The composition can be formulated as a suppository, with traditional binders and carriers such as triglycerides.

The amount of modified PA toxin, such as SEQ ID NOS: 4, 24 and 25, effective in the treatment of a particular disorder or condition, such as prostate cancer, will depend on the nature of the disorder or condition, and can be determined by standard clinical techniques. In addition, in vitro assays can be employed to identify optimal dosage ranges (see Examples 2, 4, and 5). The precise dose to be employed in the formulation will also depend on the seriousness of the disease or disorder, and should be decided according to the judgment of the practitioner and each subject's circumstances. Effective doses can be extrapolated from dose-response curves derived from in vitro or animal model test systems. Examples of effective iv doses of a modified PA toxin for a 70 kg human are about 1-10 mg of modified PA toxin, for example about 1-5 mg, for example about 1-3 mg, for example about 2.8 mg. Examples of effective intraprostatic or intratumor doses of a modified PA toxin for a 70 kg human are about 10-100 mg of modified PA toxin, for example about 10-50 mg, for example about 10-30 mg, for example about 28 mg.

The disclosure also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration. Instructions for use of the composition can also be included.

Administration of Nucleic Acid Molecules

In an example in which a nucleic acid is employed to allow expression of a nucleic acid in a cell, the nucleic acid is delivered intracellularly (e.g., by expression from a nucleic acid vector or by receptor-mediated mechanisms). In one embodiment, a nucleic acid encodes for an modified PA, such as a SEQ ID NO: 4, 24 or 25.

Various delivery systems for administering a nucleic acid are known, and include encapsulation in liposomes, microparticles, microcapsules, receptor-mediated endocytosis (Wu and Wu, *J. Biol. Chem.* 1987, 262:4429-32), and construction of therapeutic nucleic acids as part of a retroviral or other vector. Methods of introduction include, but are not limited to, intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal, vaginal and intestinal mucosa, etc.) and may be administered together with other biologically active agents. Administration can be systemic or local.

Liposomes fuse with the target site and deliver the contents of the lumen intracellularly. The liposomes are maintained in contact with the target cells for a sufficient time for fusion to occur, using various means to maintain contact, such as isolation and binding agents. Liposomes can be prepared with purified proteins or peptides that mediate fusion of membranes, such as Sendai virus or influenza virus. The lipids may be any useful combination of known liposome forming lipids, including cationic lipids, such as phosphatidylcholine. Other potential lipids include neutral lipids, such as cholesterol, phosphatidyl serine, phosphatidyl glycerol, and the like. For preparing the liposomes, the procedure described by Kato et al. (*J. Biol. Chem.* 1991, 266:3361) can be used.

Where the therapeutic molecule is a nucleic acid, administration can be achieved by an appropriate nucleic acid expression vector which is administered so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., *Proc. Natl. Acad. Sci. USA* 1991, 88:1864-8), etc. Alternatively, the nucleic acid can be introduced intracellularly and incorporated within host cell DNA for expression, by homologous recombination.

The vector pcDNA, is an example of a method of introducing the foreign cDNA into a cell under the control of a strong viral promoter (CMV) to drive the expression. However, other vectors can be used (see Example 15). Other retroviral vectors (such as pRETRO-ON, Clontech), also use this promoter but have the advantages of entering cells without any transfection aid, integrating into the genome of target cells only when the target cell is dividing (as cancer cells do, especially during first remissions after chemotherapy) and they are regulated. It is also possible to turn on the expression of a nucleic acid by administering tetracycline when these plasmids are used.

Other plasmid vectors, such as pMAM-neo (Clontech) or pMSG (Pharmacia) use the MMTV-LTR promoter (which can be regulated with steroids) or the SV10 late promoter (pSVL, Pharmacia) or metallothionein-responsive promoter (pBPV, Pharmacia) and other viral vectors, including retroviruses. Examples of other viral vectors include adenovirus, AAV (adeno-associated virus), recombinant HSV, poxviruses (vaccinia) and recombinant lentivirus (such as HIV). These vectors achieve the basic goal of delivering into the target cell the cDNA sequence and control elements needed for transcription. The present disclosure includes all forms of nucleic acid delivery, including synthetic oligos, naked DNA, plasmid and viral, integrated into the genome or not.

Having illustrated and described novel modified proaerolysin toxins, and methods of using these molecules for treating prostate cancer and metastases, it should be apparent to one skilled in the art that the disclosure can be modified in arrangement and detail without departing from such principles. In view of the many possible embodiments to which the principles of our disclosure may be applied, it should be recognized that the illustrated embodiments are only particular examples of the disclosure and should not be taken as a limitation on the scope of the disclosure. Rather, the scope of the disclosure is in accord with the following claims. We therefore claim as our invention all that comes within the scope and spirit of these claims.

We claim:

1. A purified peptide comprising the amino acid sequence shown in SEQ. ID NO:4.

2. The purified peptide of claim 1, wherein the peptide further comprises a polyhistidine tag.

3. The purified peptide of claim 2, wherein the polyhistidine tag comprises six histidines at the C-terminus of SEQ ID NO: 4.

4. A method for treating prostate cancer in a subject, comprising contacting prostate cancer cells of the subject with the peptide of claim 1.

5. The method of claim 4, wherein contacting prostate cancer cells of the subject with the peptide comprises administering the peptide to the subject.

6. The method of claim 5, wherein the peptide is administered intratumorally and/or intraprostatically.

7. The method of claim 5, wherein the peptide is administered intravenously, intramuscularly, subcutaneously, or orally.

8. The method of claim 4, wherein the subject has a localized prostate tumor.

9. The method of claim 4, wherein the subject has a metastatic prostate tumor.

10. The method of claim 4, further comprising administering granulocyte macrophage colony stimulating factor [GM-CSF] to the subject.

11. The method of claim 4, further comprising administering irradiated prostate cancer cells to the subject.

12. The method of claim 4, wherein administration results in a reduction in prostate tumor cell volume.

13. The method of claim 4, wherein administration results in a reduction of a metastatic prostate tumor.

14. The method of claim 9, wherein administration results in treatment of the metastatic prostate tumor.

15. A method for treating prostate cancer in a subject, comprising contacting prostate cancer cells of the subject with a peptide consisting of the amino acid sequence shown in SEQ ID NO:4.

16. A method for treating prostate cancer in a subject, comprising administering a peptide consisting of the amino acid sequence shown in SEQ ID NO:4 to the subject.

17. The method of claim 16, wherein the peptide is administered intratumorally and/or intraprostatically.

18. The method of claim 16, wherein the peptide is administered intravenously, intramuscularly, subcutaneously, or orally.

19. The method of claim 15, wherein the subject has a localized prostate tumor.

20. The method of claim 15, wherein the subject has a metastatic prostate tumor.

21. A method for treating prostate cancer in a subject, comprising administering the peptide of claim 2, to the subject.

22. The method of claim 21, wherein the peptide is administered intratumorally and/or intraprostatically.

23. The method of claim 21, wherein the peptide is administered intravenously, intramuscularly, subcutaneously, or orally.

24. The method of claim 21, wherein the subject has a localized prostate tumor.

25. The method of claim 21, wherein the subject has a metastatic prostate tumor.

26. A method for treating prostate cancer in a subject, comprising administering the peptide of claim 3 to the subject.

27. The method of claim 26 wherein the peptide is administered intratumorally and/or intraprostatically.

28. The method of claim 26, wherein the peptide is administered intravenously, intramuscularly, subcutaneously, or orally.

29. The method of claim 26, wherein the subject has a localized prostate tumor.

30. The method of claim 26, wherein the subject has a metastatic prostate tumor.

* * * * *

UNITED STATES PATENT AND TRADEMARK OFFICE
CERTIFICATE OF CORRECTION

PATENT NO. : 7,745,395 B2
APPLICATION NO. : 11/856543
DATED : June 29, 2010
INVENTOR(S) : Denmeade et al.

Page 1 of 1

It is certified that error appears in the above-identified patent and that said Letters Patent is hereby corrected as shown below:

Column 19, Table 1, "ADSGISSFQSSVDGAGGLRLEIPLD" should be --ADSGISSFQSSVDGAGQGLRLEIPLD--.

Column 22, lines 2-3, "$1 \times 10^{-}{}_{13}$" should be --$1 \times 10^{-13}$--.

Signed and Sealed this

Twenty-first Day of December, 2010

David J. Kappos
*Director of the United States Patent and Trademark Office*